United States Patent
Bochenko et al.

(10) Patent No.: US 12,295,913 B2
(45) Date of Patent: May 13, 2025

(54) MEDICATION CONTAINER ENCODING, VERIFICATION, AND IDENTIFICATION

(71) Applicant: CRISI Medical Systems, Inc., Franklin Lakes, NJ (US)

(72) Inventors: Walter J. Bochenko, Encinitas, CA (US); Stephen M. Prince, La Jolla, CA (US); Winthrop De Childers, San Diego, CA (US); Joseph M. Calabro, Del Mar, CA (US); Wallace S. Halliday, Del Mar, CA (US); Mark Van Veen, Cardiff, CA (US)

(73) Assignee: CRISI Medical Systems, Inc., Franklin Lakes, NJ (US)

( * ) Notice: Subject to any disclaimer, the term of this patent is extended or adjusted under 35 U.S.C. 154(b) by 1268 days.

(21) Appl. No.: 17/030,074

(22) Filed: Sep. 23, 2020

(65) Prior Publication Data

US 2021/0069061 A1    Mar. 11, 2021

Related U.S. Application Data

(63) Continuation of application No. 16/667,187, filed on Oct. 29, 2019, now Pat. No. 10,813,836, which is a
(Continued)

(51) Int. Cl.
*A61J 1/18* (2023.01)
*A61J 1/00* (2023.01)
(Continued)

(52) U.S. Cl.
CPC . *A61J 1/18* (2013.01); *A61J 1/00* (2013.01); *A61J 1/03* (2013.01); *A61J 1/1412* (2013.01); *A61J 1/2048* (2015.05); *A61J 1/2096* (2013.01); *A61J 7/04* (2013.01); *A61M 5/168* (2013.01); *B65B 3/003* (2013.01); *G06K 7/10405* (2013.01); *G06K 7/10445* (2013.01);
(Continued)

(58) Field of Classification Search
CPC ........ A61J 1/18; A61J 1/00; A61J 1/03; A61J 2205/10; A61J 2205/60; A61J 2200/30; A61J 2200/70; A51J 2200/30; A51J 2200/70; A61M 5/168; B65B 3/003; G06K 7/10405
See application file for complete search history.

(56) References Cited

U.S. PATENT DOCUMENTS

| 607,941 A | 7/1898 | Mayo |
| 614,703 A | 11/1898 | Delory |

(Continued)

FOREIGN PATENT DOCUMENTS

| EP | 1980974 A2 | 10/2008 |
| GB | 2183046 B | 11/1989 |

(Continued)

*Primary Examiner* — Daniel I Walsh
(74) *Attorney, Agent, or Firm* — The Webb Law Firm

(57) ABSTRACT

A medication container encoding, verification and identification method is provided that includes receiving data characterizing a medication, generating an identifier encapsulating the data and applying an identifier to a medication container such that it is automatically readable by a medication device. Related apparatus, systems, methods and articles are also described.

16 Claims, 21 Drawing Sheets

Related U.S. Application Data continuation of application No. 16/406,375, filed on May 8, 2019, now Pat. No. 10,492,991, which is a continuation of application No. 15/249,925, filed on Aug. 29, 2016, now Pat. No. 10,327,987, which is a continuation of application No. 13/671,752, filed on Nov. 8, 2012, now Pat. No. 9,514,131, which is a continuation-in-part of application No. 13/149,782, filed on May 31, 2011, now Pat. No. 8,328,082.

(60) Provisional application No. 61/349,878, filed on May 30, 2010.

(51) Int. Cl.
| | |
|---|---|
| A61J 1/03 | (2023.01) |
| A61J 1/14 | (2023.01) |
| A61J 1/20 | (2006.01) |
| A61J 7/04 | (2006.01) |
| A61M 5/168 | (2006.01) |
| B65B 3/00 | (2006.01) |
| G06K 7/10 | (2006.01) |
| G06K 7/14 | (2006.01) |

(52) U.S. Cl.
CPC ......... *G06K 7/1413* (2013.01); *A61J 2200/30* (2013.01); *A61J 2200/70* (2013.01); *A61J 2205/10* (2013.01); *A61J 2205/50* (2013.01); *A61J 2205/60* (2013.01)

(56) References Cited

U.S. PATENT DOCUMENTS

| | | |
|---|---|---|
| 3,430,625 A | 3/1969 | McLeod, Jr. |
| 3,816,710 A | 6/1974 | Hoffman et al. |
| 4,003,252 A | 1/1977 | Dewath |
| 4,415,802 A | 11/1983 | Long |
| 4,650,475 A | 3/1987 | Smith et al. |
| 4,835,372 A | 5/1989 | Gombrich et al. |
| 4,853,521 A | 8/1989 | Claeys et al. |
| 4,857,713 A | 8/1989 | Brown |
| 4,921,277 A | 5/1990 | McDonough |
| 4,978,335 A | 12/1990 | Arthur, III |
| 5,011,032 A | 4/1991 | Rollman |
| 5,040,422 A | 8/1991 | Frankenberger et al. |
| 5,078,683 A | 1/1992 | Sancoff et al. |
| 5,179,862 A | 1/1993 | Lynnworth |
| 5,247,826 A | 9/1993 | Frola et al. |
| 5,284,262 A | 2/1994 | O'Nan |
| 5,286,959 A | 2/1994 | Demachi |
| 5,317,506 A | 5/1994 | Coutre et al. |
| 5,338,157 A | 8/1994 | Blomquist |
| 5,429,602 A | 7/1995 | Hauser |
| 5,448,499 A | 9/1995 | Palmer |
| 5,463,906 A | 11/1995 | Spani et al. |
| 5,479,969 A | 1/1996 | Hardie et al. |
| 5,531,697 A | 7/1996 | Olsen et al. |
| 5,531,698 A | 7/1996 | Olsen |
| 5,569,212 A | 10/1996 | Brown |
| 5,611,784 A | 3/1997 | Barresi et al. |
| 5,612,524 A | 3/1997 | Sant'Anselmo et al. |
| 5,628,309 A | 5/1997 | Brown |
| 5,651,775 A | 7/1997 | Walker et al. |
| 5,692,640 A | 12/1997 | Caulfield et al. |
| 5,713,856 A | 2/1998 | Eggers et al. |
| 5,720,733 A | 2/1998 | Brown |
| 5,740,428 A | 4/1998 | Mortimore et al. |
| 5,781,442 A | 7/1998 | Engleson et al. |
| 5,782,814 A | 7/1998 | Brown et al. |
| 5,792,117 A | 8/1998 | Brown |
| 5,841,846 A | 11/1998 | Abbruscato et al. |
| 5,845,264 A | 12/1998 | Nellhaus |
| 5,873,731 A | 2/1999 | Prendergast |
| 5,882,338 A | 3/1999 | Gray |
| 5,883,370 A | 3/1999 | Walker et al. |
| 5,907,493 A | 5/1999 | Boyer et al. |
| 5,920,263 A | 7/1999 | Huttenhoff et al. |
| 5,925,014 A | 7/1999 | Teeple, Jr. |
| 6,039,251 A | 3/2000 | Holowko et al. |
| 6,098,892 A | 8/2000 | Peoples, Jr. |
| 6,106,498 A | 8/2000 | Friedli et al. |
| 6,123,686 A | 9/2000 | Olsen et al. |
| 6,155,485 A | 12/2000 | Coughlin et al. |
| 6,189,727 B1 | 2/2001 | Shoenfeld |
| D438,634 S | 3/2001 | Merry |
| 6,249,299 B1 | 6/2001 | Tainer |
| 6,256,037 B1 | 7/2001 | Callahan |
| 6,270,455 B1 | 8/2001 | Brown |
| 6,277,099 B1 | 8/2001 | Strowe et al. |
| 6,341,174 B1 | 1/2002 | Callahan et al. |
| 6,342,889 B1 | 1/2002 | Callahan |
| 6,381,029 B1 | 4/2002 | Tipirneni |
| 6,422,094 B1 | 7/2002 | Ganshorn |
| 6,437,316 B1 | 8/2002 | Colman et al. |
| RE37,829 E * | 9/2002 | Charhut ................. G16H 20/13 221/9 |
| 6,464,667 B1 | 10/2002 | Kamen et al. |
| 6,468,424 B1 | 10/2002 | Donig et al. |
| 6,471,089 B2 | 10/2002 | Liff et al. |
| 6,482,185 B1 | 11/2002 | Hartmann |
| 6,519,569 B1 | 2/2003 | White et al. |
| 6,535,637 B1 * | 3/2003 | Wootton ................. B65B 57/00 221/102 |
| 6,579,231 B1 | 6/2003 | Phipps |
| RE38,189 E | 7/2003 | Walker et al. |
| 6,626,355 B2 | 9/2003 | Sasse et al. |
| 6,641,562 B1 | 11/2003 | Peterson |
| 6,644,130 B2 | 11/2003 | Imai et al. |
| 6,659,338 B1 | 12/2003 | Dittmann et al. |
| 6,671,563 B1 | 12/2003 | Engleson et al. |
| 6,675,660 B1 | 1/2004 | Mosier et al. |
| 6,685,227 B2 | 2/2004 | Merry et al. |
| 6,685,678 B2 | 2/2004 | Evans et al. |
| 6,697,067 B1 | 2/2004 | Callahan et al. |
| 6,731,989 B2 | 5/2004 | Engleson et al. |
| 6,733,495 B1 | 5/2004 | Bek et al. |
| 6,742,992 B2 | 6/2004 | Davis |
| 6,798,533 B2 | 9/2004 | Tipirneni |
| 6,825,864 B2 | 11/2004 | Botten et al. |
| 6,851,651 B2 | 2/2005 | Goodzeit |
| 6,854,338 B2 | 2/2005 | Khuri-Yakub et al. |
| 6,915,170 B2 | 7/2005 | Engleson et al. |
| 6,985,870 B2 | 1/2006 | Martucci et al. |
| 6,993,402 B2 | 1/2006 | Klass et al. |
| 7,000,485 B2 | 2/2006 | Ao et al. |
| 7,061,831 B2 | 6/2006 | De La Huerga |
| 7,074,205 B1 | 7/2006 | Duffy et al. |
| 7,074,209 B2 | 7/2006 | Evans et al. |
| 7,096,072 B2 | 8/2006 | Engleson et al. |
| 7,103,419 B2 | 9/2006 | Engleson et al. |
| 7,106,479 B2 | 9/2006 | Roy et al. |
| 7,107,106 B2 | 9/2006 | Engleson et al. |
| 7,115,113 B2 | 10/2006 | Evans et al. |
| 7,116,343 B2 | 10/2006 | Botten et al. |
| 7,161,488 B2 | 1/2007 | Frasch |
| 7,171,277 B2 | 1/2007 | Engleson et al. |
| 7,175,081 B2 | 2/2007 | Andreasson et al. |
| 7,180,624 B2 | 2/2007 | Tipirneni |
| 7,182,256 B2 | 2/2007 | Andreasson et al. |
| 7,225,683 B2 | 6/2007 | Harnett et al. |
| 7,236,936 B2 | 6/2007 | White et al. |
| 7,237,199 B1 | 6/2007 | Menhardt et al. |
| 7,256,682 B2 | 8/2007 | Sweeny, II |
| 7,264,323 B2 | 9/2007 | Tainer et al. |
| 7,298,274 B2 | 11/2007 | Chen et al. |
| 7,299,981 B2 | 11/2007 | Hickle et al. |
| 7,319,540 B2 | 1/2008 | Tipirneni |
| 7,322,525 B2 | 1/2008 | Itoh |
| 7,347,841 B2 | 3/2008 | Elhadad et al. |
| 7,358,505 B2 | 4/2008 | Woodworth et al. |
| 7,360,448 B2 | 4/2008 | Maginnis et al. |
| 7,364,067 B2 | 4/2008 | Steusloff et al. |

(56) References Cited

U.S. PATENT DOCUMENTS

| | | | |
|---|---|---|---|
| 7,370,797 B1* | 5/2008 | Sullivan | G06K 17/00 235/472.01 |
| 7,375,737 B2 | 5/2008 | Botten et al. | |
| 7,384,410 B2 | 6/2008 | Eggers et al. | |
| 7,442,181 B2 | 10/2008 | Schubert et al. | |
| 7,469,598 B2 | 12/2008 | Shkarlet et al. | |
| 7,469,599 B2 | 12/2008 | Froehlich et al. | |
| 7,483,756 B2 | 1/2009 | Engleson et al. | |
| D588,200 S | 3/2009 | Langan et al. | |
| 7,534,239 B1 | 5/2009 | Schneider et al. | |
| D593,613 S | 6/2009 | Langan et al. | |
| D595,361 S | 6/2009 | Langan et al. | |
| 7,559,483 B2 | 7/2009 | Hickle et al. | |
| 7,564,579 B2 | 7/2009 | Tipirneni | |
| D597,608 S | 8/2009 | Langan et al. | |
| D602,534 S | 10/2009 | Langan et al. | |
| 7,614,545 B2* | 11/2009 | Christoffersen | G06K 1/12 235/487 |
| 7,617,739 B1 | 11/2009 | Dam | |
| D605,228 S | 12/2009 | Langan et al. | |
| D605,229 S | 12/2009 | Langan et al. | |
| D605,230 S | 12/2009 | Langan et al. | |
| 7,645,258 B2 | 1/2010 | White et al. | |
| 7,673,527 B2 | 3/2010 | Ehring et al. | |
| 7,694,565 B2 | 4/2010 | Koerdt et al. | |
| 7,703,336 B2 | 4/2010 | Genosar | |
| 7,704,231 B2 | 4/2010 | Pongpairochana et al. | |
| 7,753,880 B2 | 7/2010 | Malackowski | |
| 7,753,891 B2 | 7/2010 | Tennican et al. | |
| 7,756,724 B2 | 7/2010 | Gropper et al. | |
| 7,763,006 B2 | 7/2010 | Tennican | |
| D621,879 S | 8/2010 | Langan et al. | |
| D621,880 S | 8/2010 | Langan et al. | |
| 7,771,385 B2 | 8/2010 | Eggers et al. | |
| D624,595 S | 9/2010 | Langan et al. | |
| D624,596 S | 9/2010 | Langan et al. | |
| 7,799,010 B2 | 9/2010 | Tennican | |
| 7,813,939 B2 | 10/2010 | Clements et al. | |
| 7,814,123 B2 | 10/2010 | Conner et al. | |
| 7,815,605 B2 | 10/2010 | Souter | |
| 7,819,838 B2 | 10/2010 | Ziegler et al. | |
| 7,822,096 B2 | 10/2010 | Kuksenkov | |
| 7,859,473 B2 | 12/2010 | Gibson | |
| D633,151 S | 2/2011 | Langan et al. | |
| 7,887,513 B2 | 2/2011 | Nemoto et al. | |
| D634,367 S | 3/2011 | Langan et al. | |
| D634,368 S | 3/2011 | Langan et al. | |
| D634,369 S | 3/2011 | Langan et al. | |
| 7,905,861 B2 | 3/2011 | Rhinehart et al. | |
| 7,918,830 B2 | 4/2011 | Langan et al. | |
| 7,922,073 B2 | 4/2011 | de la Huerga | |
| 7,927,313 B2 | 4/2011 | Stewart et al. | |
| 7,933,780 B2 | 4/2011 | De La Huerga | |
| 7,941,949 B2 | 5/2011 | Cloninger | |
| D639,861 S | 6/2011 | Langan et al. | |
| D639,862 S | 6/2011 | Langan et al. | |
| D639,863 S | 6/2011 | Langan et al. | |
| 7,967,778 B2 | 6/2011 | Nemoto et al. | |
| D641,421 S | 7/2011 | Langan et al. | |
| D641,422 S | 7/2011 | Langan et al. | |
| 7,976,508 B2 | 7/2011 | Hoag | |
| D643,468 S | 8/2011 | Langan et al. | |
| D643,469 S | 8/2011 | Langan et al. | |
| D643,470 S | 8/2011 | Langan et al. | |
| D643,471 S | 8/2011 | Langan et al. | |
| D643,472 S | 8/2011 | Langan et al. | |
| 7,991,627 B2 | 8/2011 | Hutchinson et al. | |
| 8,002,736 B2* | 8/2011 | Patrick | A61B 8/0841 604/82 |
| D645,094 S | 9/2011 | Langan et al. | |
| 8,031,347 B2 | 10/2011 | Edwards et al. | |
| D649,196 S | 11/2011 | Langan et al. | |
| 8,063,925 B2 | 11/2011 | Tipirneni | |
| 8,065,924 B2 | 11/2011 | Ziegler et al. | |
| 8,069,060 B2 | 11/2011 | Tipirneni | |
| 8,099,304 B2* | 1/2012 | Maughan | G16H 50/20 705/3 |
| 8,111,159 B2 | 2/2012 | Andreasson et al. | |
| 8,133,178 B2 | 3/2012 | Brauker et al. | |
| 8,140,349 B2 | 3/2012 | Hanson et al. | |
| 8,221,356 B2 | 7/2012 | Enggaard et al. | |
| 8,235,938 B2 | 8/2012 | Eggers et al. | |
| 8,240,550 B2 | 8/2012 | Steusloff et al. | |
| 8,303,547 B2 | 11/2012 | Brown | |
| 8,328,082 B1* | 12/2012 | Bochenko | G16H 10/40 235/462.15 |
| 8,355,753 B2 | 1/2013 | Bochenko et al. | |
| 8,385,972 B2 | 2/2013 | Bochenko et al. | |
| 8,394,053 B2 | 3/2013 | Bochenko et al. | |
| 8,480,834 B2 | 7/2013 | Rice et al. | |
| 8,505,809 B2 | 8/2013 | Steusloff et al. | |
| 8,606,596 B1* | 12/2013 | Bochenko | G06Q 10/00 705/2 |
| 8,636,202 B2 | 1/2014 | Keefe et al. | |
| 8,639,521 B2 | 1/2014 | Eggers et al. | |
| 8,639,525 B2 | 1/2014 | Levine et al. | |
| 8,645,154 B2 | 2/2014 | Eggers et al. | |
| 8,702,674 B2 | 4/2014 | Bochenko | |
| 8,720,772 B2 | 5/2014 | Colman et al. | |
| 8,752,088 B1 | 6/2014 | Harvey et al. | |
| 8,945,066 B2 | 2/2015 | Bochenko et al. | |
| 9,039,655 B2 | 5/2015 | Prince et al. | |
| 9,078,809 B2 | 7/2015 | Bochenko et al. | |
| 9,101,534 B2 | 8/2015 | Bochenko | |
| 9,514,131 B1* | 12/2016 | Bochenko | G16H 10/40 |
| 9,931,498 B2 | 4/2018 | Bochenko | |
| 10,127,421 B1 | 11/2018 | Vercalli et al. | |
| 10,143,830 B2 | 12/2018 | Bochenko | |
| 10,327,987 B1 | 6/2019 | Bochenko et al. | |
| 1,042,991 A1 | 12/2019 | Bochenko et al. | |
| 2001/0020148 A1 | 9/2001 | Sasse et al. | |
| 2001/0027634 A1 | 10/2001 | Hebron et al. | |
| 2001/0028308 A1 | 10/2001 | De La Huerga | |
| 2001/0049608 A1 | 12/2001 | Hochman | |
| 2001/0056258 A1 | 12/2001 | Evans | |
| 2002/0017784 A1 | 2/2002 | Merry et al. | |
| 2002/0022821 A1 | 2/2002 | Eilersen | |
| 2002/0040208 A1 | 4/2002 | Flaherty et al. | |
| 2002/0077852 A1 | 6/2002 | Ford et al. | |
| 2002/0088131 A1 | 7/2002 | Baxa et al. | |
| 2002/0093189 A1 | 7/2002 | Krupa | |
| 2002/0096261 A1 | 7/2002 | Yang | |
| 2002/0098126 A1 | 7/2002 | Day | |
| 2002/0099334 A1 | 7/2002 | Hanson et al. | |
| 2002/0101656 A1 | 8/2002 | Blumenthal et al. | |
| 2002/0148893 A1 | 10/2002 | Walsh et al. | |
| 2002/0188259 A1 | 12/2002 | Hickle et al. | |
| 2002/0195488 A1 | 12/2002 | Walsh | |
| 2003/0041565 A1 | 3/2003 | Banks et al. | |
| 2003/0052788 A1 | 3/2003 | Kwong-Tai Chung | |
| 2003/0055685 A1 | 3/2003 | Cobb et al. | |
| 2003/0061750 A1 | 4/2003 | Bernier et al. | |
| 2003/0078893 A1 | 4/2003 | Shah et al. | |
| 2003/0086338 A1 | 5/2003 | Sastry et al. | |
| 2003/0101143 A1 | 5/2003 | Montgomery et al. | |
| 2003/0135388 A1 | 7/2003 | Martucci et al. | |
| 2003/0139701 A1 | 7/2003 | White et al. | |
| 2003/0160698 A1 | 8/2003 | Andreasson et al. | |
| 2003/0164401 A1 | 9/2003 | Andreasson et al. | |
| 2003/0174326 A1 | 9/2003 | Rzasa et al. | |
| 2003/0192468 A1 | 10/2003 | Goertzen | |
| 2003/0204359 A1 | 10/2003 | Blakley | |
| 2004/0007330 A1 | 1/2004 | Jones | |
| 2004/0082918 A1 | 4/2004 | Evans et al. | |
| 2004/0088187 A1 | 5/2004 | Chudy et al. | |
| 2004/0103951 A1 | 6/2004 | Osborne et al. | |
| 2004/0105115 A1 | 6/2004 | Edwards et al. | |
| 2004/0123565 A1 | 7/2004 | Rice et al. | |
| 2004/0172283 A1 | 9/2004 | Vanderveen et al. | |
| 2004/0179051 A1 | 9/2004 | Tainer et al. | |
| 2004/0179132 A1 | 9/2004 | Fujino et al. | |
| 2004/0193453 A1 | 9/2004 | Butterfield et al. | |
| 2004/0212834 A1 | 10/2004 | Edwards et al. | |
| 2004/0225528 A1 | 11/2004 | Brock | |

(56) References Cited

U.S. PATENT DOCUMENTS

| | | |
|---|---|---|
| 2004/0228641 A1 | 11/2004 | Rommelmann et al. |
| 2004/0238631 A1 | 12/2004 | Andreasson et al. |
| 2004/0257428 A1 | 12/2004 | Sato et al. |
| 2005/0038558 A1 | 2/2005 | Keene |
| 2005/0055242 A1 | 3/2005 | Bello et al. |
| 2005/0070978 A1 | 3/2005 | Bek et al. |
| 2005/0071044 A1 | 3/2005 | Yonge et al. |
| 2005/0088306 A1 | 4/2005 | Andreasson et al. |
| 2005/0101905 A1 | 5/2005 | Merry |
| 2005/0118048 A1 | 6/2005 | Traxinger |
| 2005/0125097 A1 | 6/2005 | Chudy et al. |
| 2005/0134460 A1 | 6/2005 | Usami |
| 2005/0151652 A1 | 7/2005 | Frasch |
| 2005/0151823 A1 | 7/2005 | Botten et al. |
| 2005/0154368 A1 | 7/2005 | Lim et al. |
| 2005/0165559 A1 | 7/2005 | Nelson |
| 2005/0167026 A1 | 8/2005 | Dronzek et al. |
| 2005/0171813 A1 | 8/2005 | Jordan |
| 2005/0199723 A1 | 9/2005 | Lubow |
| 2005/0224137 A1 | 10/2005 | Tribble et al. |
| 2005/0240441 A1 | 10/2005 | Suzuki et al. |
| 2005/0242950 A1 | 11/2005 | Lindsay et al. |
| 2005/0246202 A1 * | 11/2005 | Hyoudou ............... G16H 50/20 235/375 |
| 2005/0277873 A1 | 12/2005 | Stewart et al. |
| 2005/0277890 A1 | 12/2005 | Stewart et al. |
| 2005/0279419 A1 | 12/2005 | Tribble et al. |
| 2006/0032918 A1 | 2/2006 | Andreasson et al. |
| 2006/0041330 A1 * | 2/2006 | Ansari ............... G06Q 10/087 700/240 |
| 2006/0065713 A1 | 3/2006 | Kingery |
| 2006/0079843 A1 | 4/2006 | Brooks et al. |
| 2006/0102503 A1 | 5/2006 | Elhadad et al. |
| 2006/0143051 A1 | 6/2006 | Eggers et al. |
| 2006/0144942 A1 | 7/2006 | Evans et al. |
| 2006/0152367 A1 * | 7/2006 | Narayanaswamy ... G06Q 10/08 340/572.1 |
| 2006/0178617 A1 | 8/2006 | Adams et al. |
| 2006/0189895 A1 | 8/2006 | Neel et al. |
| 2006/0190302 A1 | 8/2006 | Eggers et al. |
| 2006/0206356 A1 | 9/2006 | Vanderveen |
| 2006/0224125 A1 | 10/2006 | Simpson et al. |
| 2006/0229551 A1 | 10/2006 | Martinez et al. |
| 2006/0253346 A1 | 11/2006 | Gomez |
| 2006/0270997 A1 | 11/2006 | Lim et al. |
| 2006/0277269 A1 | 12/2006 | Dent et al. |
| 2006/0287887 A1 | 12/2006 | Hutchinson et al. |
| 2007/0008399 A1 | 1/2007 | Botten et al. |
| 2007/0008523 A1 * | 1/2007 | Kaye ............... G01N 21/359 356/300 |
| 2007/0029110 A1 | 2/2007 | Matsumoto et al. |
| 2007/0085697 A1 | 4/2007 | Breed |
| 2007/0100316 A1 | 5/2007 | Traxinger |
| 2007/0126578 A1 | 6/2007 | Broussard |
| 2007/0134044 A1 | 6/2007 | Colbrunn et al. |
| 2007/0167919 A1 | 7/2007 | Nemoto et al. |
| 2007/0179448 A1 | 8/2007 | Lim et al. |
| 2007/0186923 A1 | 8/2007 | Poutiatine et al. |
| 2007/0187475 A1 | 8/2007 | MacLeod |
| 2007/0191787 A1 | 8/2007 | Lim et al. |
| 2007/0204497 A1 | 9/2007 | de la Huerga |
| 2007/0255199 A1 | 11/2007 | Dewey |
| 2007/0278786 A1 | 12/2007 | Mezhinsky et al. |
| 2007/0280710 A1 | 12/2007 | Tainer et al. |
| 2007/0293830 A1 | 12/2007 | Martin |
| 2007/0293982 A1 | 12/2007 | Rosenblum |
| 2008/0043088 A1 | 2/2008 | Botten et al. |
| 2008/0051937 A1 | 2/2008 | Khan et al. |
| 2008/0053560 A1 | 3/2008 | Hartman et al. |
| 2008/0071219 A1 | 3/2008 | Rhinehart et al. |
| 2008/0118141 A1 | 5/2008 | Sommer et al. |
| 2008/0177568 A1 | 7/2008 | Kotidis |
| 2008/0188814 A1 | 8/2008 | Lavi-Loebl et al. |
| 2008/0191013 A1 | 8/2008 | Liberatore |
| 2008/0243088 A1 | 10/2008 | Evans |
| 2008/0255523 A1 | 10/2008 | Grinberg |
| 2008/0283050 A1 | 11/2008 | Faram |
| 2008/0288105 A1 | 11/2008 | Mauger et al. |
| 2008/0288287 A1 | 11/2008 | Stanners |
| 2008/0294108 A1 | 11/2008 | Briones et al. |
| 2008/0301982 A1 | 12/2008 | Kaufman |
| 2008/0306439 A1 | 12/2008 | Nelson et al. |
| 2008/0314978 A1 * | 12/2008 | Fedorko ............... G16H 70/40 235/385 |
| 2009/0043253 A1 | 2/2009 | Podaima |
| 2009/0085768 A1 | 4/2009 | Patel et al. |
| 2009/0112178 A1 | 4/2009 | Behzadi |
| 2009/0112333 A1 | 4/2009 | Sahai |
| 2009/0126483 A1 | 5/2009 | Blendinger et al. |
| 2009/0126825 A1 * | 5/2009 | Eliuk ............... B65B 3/003 141/330 |
| 2009/0126866 A1 | 5/2009 | Stenner et al. |
| 2009/0137956 A1 | 5/2009 | Souter |
| 2009/0143673 A1 | 6/2009 | Drost et al. |
| 2009/0149744 A1 | 6/2009 | Nemoto et al. |
| 2009/0156931 A1 | 6/2009 | Nemoto et al. |
| 2009/0159654 A1 | 6/2009 | Grimard |
| 2009/0164238 A1 | 6/2009 | Auchinleck |
| 2009/0173779 A1 | 7/2009 | Szesko et al. |
| 2009/0200185 A1 | 8/2009 | Follman et al. |
| 2009/0259176 A1 | 10/2009 | Yairi |
| 2009/0277570 A1 | 11/2009 | Caveney et al. |
| 2009/0288497 A1 | 11/2009 | Ziegler et al. |
| 2009/0296540 A1 | 12/2009 | Gilbert et al. |
| 2009/0306620 A1 | 12/2009 | Gilbert et al. |
| 2010/0012018 A1 | 1/2010 | Ribi |
| 2010/0022953 A1 | 1/2010 | Bochenko et al. |
| 2010/0022987 A1 | 1/2010 | Bochenko et al. |
| 2010/0036310 A1 | 2/2010 | Hillman |
| 2010/0036313 A1 | 2/2010 | Shener et al. |
| 2010/0065633 A1 | 3/2010 | Nelson et al. |
| 2010/0065643 A1 | 3/2010 | Leyvraz et al. |
| 2010/0076310 A1 | 3/2010 | Wenderow et al. |
| 2010/0095782 A1 | 4/2010 | Ferencz et al. |
| 2010/0108763 A1 | 5/2010 | Verhoeven |
| 2010/0114680 A1 | 5/2010 | Steelberg et al. |
| 2010/0114951 A1 | 5/2010 | Bauman et al. |
| 2010/0116365 A1 | 5/2010 | McCarty |
| 2010/0145165 A1 | 6/2010 | Merry |
| 2010/0176146 A1 | 7/2010 | Ben-Dor |
| 2010/0179417 A1 | 7/2010 | Russo |
| 2010/0204659 A1 | 8/2010 | Bochenko et al. |
| 2010/0280486 A1 | 11/2010 | Khair et al. |
| 2010/0286599 A1 | 11/2010 | Ziegler et al. |
| 2010/0305499 A1 | 12/2010 | Matsiev et al. |
| 2010/0305750 A1 | 12/2010 | Conley |
| 2011/0009800 A1 | 1/2011 | Dam et al. |
| 2011/0009817 A1 | 1/2011 | Bennett et al. |
| 2011/0028937 A1 | 2/2011 | Powers et al. |
| 2011/0060198 A1 | 3/2011 | Bennett et al. |
| 2011/0062703 A1 * | 3/2011 | Lopez ............... A61J 1/201 285/129.1 |
| 2011/0093279 A1 | 4/2011 | Levine et al. |
| 2011/0111794 A1 | 5/2011 | Bochenko et al. |
| 2011/0112473 A1 | 5/2011 | Bochenko et al. |
| 2011/0112474 A1 * | 5/2011 | Bochenko ............ A61M 39/02 604/68 |
| 2011/0137288 A1 | 6/2011 | Tallarida et al. |
| 2011/0152824 A1 | 6/2011 | DiPerna et al. |
| 2011/0152825 A1 | 6/2011 | Marggi |
| 2011/0152834 A1 | 6/2011 | Langan et al. |
| 2011/0160655 A1 | 6/2011 | Hanson et al. |
| 2011/0161112 A1 | 6/2011 | Keefe et al. |
| 2011/0166511 A1 | 7/2011 | Sharvit et al. |
| 2011/0176490 A1 | 7/2011 | Mehta et al. |
| 2011/0178359 A1 | 7/2011 | Hirschman et al. |
| 2011/0185821 A1 | 8/2011 | Genosar |
| 2011/0259954 A1 | 10/2011 | Bartz et al. |
| 2011/0264069 A1 * | 10/2011 | Bochenko ............ A61J 1/2096 604/404 |
| 2011/0313349 A1 | 12/2011 | Krulevitch et al. |
| 2011/0315611 A1 | 12/2011 | Fulkerson et al. |
| 2012/0004542 A1 | 1/2012 | Nemoto et al. |
| 2012/0004602 A1 | 1/2012 | Hanson et al. |

(56) References Cited

U.S. PATENT DOCUMENTS

| | | |
|---|---|---|
| 2012/0004637 A1 | 1/2012 | Krulevitch et al. |
| 2012/0006127 A1 | 1/2012 | Nielsen |
| 2012/0022458 A1 | 1/2012 | Oh et al. |
| 2012/0035535 A1 | 2/2012 | Johnson et al. |
| 2012/0037266 A1* | 2/2012 | Bochenko ............ A61J 1/2096 |
| | | 604/404 |
| 2012/0041416 A1 | 2/2012 | Lal |
| 2012/0046295 A1 | 2/2012 | Charrier et al. |
| 2012/0065617 A1 | 3/2012 | Matsiev et al. |
| 2012/0089411 A1 | 4/2012 | Srnka et al. |
| 2012/0095415 A1 | 4/2012 | Sharvit et al. |
| 2012/0127290 A1 | 5/2012 | Tojo et al. |
| 2012/0153031 A1 | 6/2012 | Rupp |
| 2012/0199601 A1 | 8/2012 | Sawa |
| 2012/0203647 A1 | 8/2012 | Smith |
| 2012/0222468 A1* | 9/2012 | Nelson ................ A61M 5/168 |
| | | 73/61.41 |
| 2012/0226446 A1 | 9/2012 | Nelson et al. |
| 2012/0226447 A1 | 9/2012 | Nelson et al. |
| 2012/0241043 A1 | 9/2012 | Perazzo et al. |
| 2012/0287431 A1 | 11/2012 | Matsiev et al. |
| 2012/0299468 A1 | 11/2012 | Tsai et al. |
| 2012/0323208 A1* | 12/2012 | Bochenko ............ G16H 20/10 |
| | | 604/404 |
| 2012/0325330 A1* | 12/2012 | Prince ............... A61M 5/16881 |
| | | 137/455 |
| 2013/0012908 A1 | 1/2013 | Yeung |
| 2013/0018256 A1 | 1/2013 | Kislev et al. |
| 2013/0018356 A1* | 1/2013 | Prince ................ G06Q 10/0833 |
| | | 604/506 |
| 2013/0023851 A1 | 1/2013 | Maier et al. |
| 2013/0041258 A1* | 2/2013 | Patrick ............... A61M 5/16827 |
| | | 600/439 |
| 2013/0092727 A1 | 4/2013 | Edwards et al. |
| 2013/0096511 A1 | 4/2013 | MacArthur |
| 2013/0105568 A1* | 5/2013 | Jablonski ............ G16H 20/10 |
| | | 235/375 |
| 2013/0158481 A1 | 6/2013 | Taylor |
| 2013/0181046 A1 | 7/2013 | Fedorko et al. |
| 2013/0204227 A1* | 8/2013 | Bochenko ............ G16H 10/60 |
| | | 604/189 |
| 2013/0225945 A1 | 8/2013 | Prince et al. |
| 2013/0226137 A1 | 8/2013 | Brown |
| 2013/0289496 A1 | 10/2013 | Langan et al. |
| 2013/0327822 A1* | 12/2013 | Keefe ................. G16H 20/13 |
| | | 235/375 |
| 2014/0039383 A1 | 2/2014 | Dobbles et al. |
| 2014/0060729 A1 | 3/2014 | Srnka et al. |
| 2014/0066880 A1* | 3/2014 | Prince ................ G16H 20/17 |
| | | 604/500 |
| 2014/0095187 A1* | 4/2014 | Greenman ........... G16H 15/00 |
| | | 705/2 |
| 2014/0128832 A1 | 5/2014 | Prince et al. |
| 2014/0142975 A1 | 5/2014 | Keefe et al. |
| 2014/0263064 A1* | 9/2014 | Jones ................ A61M 1/36222 |
| | | 73/61.41 |
| 2014/0276213 A1* | 9/2014 | Bochenko ........... A61M 39/162 |
| | | 600/573 |
| 2014/0297313 A1* | 10/2014 | Condurso .............. G16H 20/10 |
| | | 705/2 |
| 2014/0303606 A1 | 10/2014 | Garner-Richards et al. |
| 2014/0318078 A1* | 10/2014 | Kondo .................. G16H 20/13 |
| | | 382/141 |
| 2014/0361076 A1* | 12/2014 | Iantorno ............. G07F 17/0092 |
| | | 235/381 |
| 2015/0120320 A1 | 4/2015 | Fateh |
| 2015/0204705 A1 | 7/2015 | Forster et al. |
| 2015/0211904 A1 | 7/2015 | Forster |
| 2015/0223732 A1 | 8/2015 | Prince et al. |
| 2015/0224497 A1 | 8/2015 | Furrer et al. |
| 2015/0248634 A1 | 9/2015 | Vollm et al. |
| 2015/0254424 A1 | 9/2015 | Zehler |
| 2016/0003733 A1 | 1/2016 | Goldberg et al. |
| 2016/0158108 A1* | 6/2016 | Gofer ........................ A61J 1/03 |
| | | 206/539 |
| 2016/0328535 A1 | 11/2016 | Barr |
| 2016/0355322 A1* | 12/2016 | Burton, Jr. ............ A61J 7/0481 |
| 2017/0065809 A1 | 3/2017 | Bochenko |
| 2017/0091502 A1 | 3/2017 | Furlong et al. |
| 2017/0095405 A1 | 4/2017 | Afsarifard et al. |
| 2017/0172527 A1 | 6/2017 | Uber, III |
| 2017/0316298 A1 | 11/2017 | Chu |
| 2018/0028406 A1 | 2/2018 | Patton et al. |
| 2018/0147346 A1* | 5/2018 | Grosse-Wentrup .......................... |
| | | A61M 5/14232 |
| 2018/0336383 A1 | 11/2018 | Roth |
| 2018/0344927 A1 | 12/2018 | Khan |
| 2019/0209433 A1 | 7/2019 | Fateh et al. |
| 2019/0262231 A1* | 8/2019 | Bochenko ................ A61J 1/03 |
| 2020/0335195 A1* | 10/2020 | Fryman ................ A61M 5/484 |
| 2021/0069061 A1* | 3/2021 | Bochenko ................ A61J 7/04 |
| 2021/0183489 A1* | 6/2021 | Monirabbasi ......... G06F 1/3215 |
| 2022/0305202 A1* | 9/2022 | Rosinko ............. G06Q 30/0633 |
| 2023/0119186 A1* | 4/2023 | O'Donoghue ........... G06N 3/08 |
| | | 706/21 |
| 2023/0225947 A1* | 7/2023 | Zuleta .................. A61J 7/0427 |
| | | 221/2 |
| 2023/0256146 A1* | 8/2023 | Prindle ................. A61M 5/172 |
| | | 604/5.04 |
| 2023/0302224 A1* | 9/2023 | Prince .................... G16H 20/10 |

FOREIGN PATENT DOCUMENTS

| | | |
|---|---|---|
| GB | 2275123 | 8/1994 |
| GB | 2504288 A | 1/2014 |
| GB | 2504295 A | 1/2014 |
| GB | 2504297 A | 1/2014 |
| JP | 2011184080 A | 9/2011 |
| WO | 2009114115 A1 | 9/2009 |
| WO | 2010144482 A2 | 12/2010 |
| WO | 2012034084 A2 | 3/2012 |
| WO | 2014016311 A1 | 1/2014 |
| WO | 2014016316 A1 | 1/2014 |

* cited by examiner

MEDICATION CONTAINER ENCODING, VERIFICATION, AND IDENTIFICATION

CROSS-REFERENCE TO RELATED APPLICATIONS

This application is a continuation of U.S. patent application Ser. No. 16/667,187 filed Oct. 29, 2019, which is a continuation of U.S. patent application Ser. No. 16/406,375 filed May 8, 2019 (now U.S. Pat. No. 10,492,991), which is a continuation of U.S. patent application Ser. No. 15/249,925 filed on Aug. 29, 2016 (now U.S. Pat. No. 10,327,987), which is a continuation of U.S. patent application Ser. No. 13/671,752 filed on Nov. 8, 2012 (now U.S. Pat. No. 9,514,131), which is a continuation-in-part of U.S. patent application Ser. No. 13/149,782 filed on May 31, 2011 (now U.S. Pat. No. 8,328,082), which claims priority to U.S. Prov. Pat. App. Ser. No. 61/349,878 filed on May 30, 2010, the contents of which are all hereby fully incorporated by reference.

FIELD

The subject matter described herein relates to a medication identification, encoding and verification methodology for use in scanning, verifying and/or marking medication containers so the medications in those containers can be properly identified and documented during the process of patient medication preparation, administration, and disposal. Medication containers can include syringes, bags, vials, medication transfer apparatus as well as medical packaging with marking applied during various manufacturing and pharmacy processes.

BACKGROUND

Many health care procedures involving the preparation, administration and wasting of medication involve a clinician manually reading labeling applied to various medication containers. The current practice of relying on manual reading of labels is prone to user errors resulting in overmedication, under-medication, administration of non-compatible medications and/or administration of medications to which a patient is allergic. In addition, problems also arise in properly labeling medication containers during manufacture and preparation (whether in the pharmacy or otherwise). Proper labeling is of particular importance when there are multiple components bundled together.

SUMMARY

In one aspect, first data that comprises at least one optical identifier is generated or received. The at least one optical identifier encapsulates second data (which can be the same or different from the first data) characterizing at least one medication. The at least one optical identifier is applied to the outer surface of a tip portion of a medication container such that the at least one identifier is positioned to be automatically read by at least one optical sensor of a medication device along the outer surface of the tip portion when the medication container rotatably mates with a complementary fitting on the medication device.

The at least one optical sensor of the medication device and automatically read one or more of the at least one optical identifier when the medication container rotatable mates with a complementary fitting on the medication device. The medication device can include an injection port through which medication within the medication container is received by the medication device. The medication device can be a medication administration device for administering medication within the medication container to a patient. The medication device can be a medication wasting device for disposal of unused medication within the medication container.

In some variations, the medication is rotated concurrently with the applying of the at least one optical identifier. The at least one optical identifier can be adhered to the medication container and/or etched on the medication container.

Additional data can be received (e.g., third data) that characterizes medication within a medication container. Such data can be used to generate the at least one optical identifier. The additional data can be received via many sources including, but not limited to, scanning a different optical identifier, receiving data from a remote data source via a fixed or wireless communications network, and/or receiving user-generated input via a graphical user interface.

The at least one optical identifier can encapsulate diverse data including, for example, a name of the medication and a concentration of the medication and/or a location accessible via a communications network to retrieve more information and/or a short code for one or more characteristics of medication.

The medication container can be a syringe having a barrel portion and a fluid outlet on the tip portion. The tip portion can include a cylindrical or conical outer surface terminating at the fluid outlet and the at least one optical identifier is applied to the outer surface. The tip portion can include a Luer lock fitting and the at least one optical identifier can be positioned on the Luer lock fitting.

The medication container can be a vial having a stopper on the tip portion and the at least one optical identifier can be applied to the stopper or a corresponding stopper closure.

The medication container can be a medication bag containing a medication solution having a Luer fitting on the tip portion such that the at least one optical identifier is applied to the Luer fitting.

The medication container can be a medication bag containing a medication solution and having a spikeable port on the tip portion such that the at least one optical identifier is applied to the spikeable port.

The medication container can be an envelope having a Luer fitting on the tip portion such that the at least one optical identifier is applied to the Luer fitting.

The medication container can be an envelope having a tubing set extending from the tip portion such that the identifier is applied to the tubing set.

The medication container can be a fluid transfer device facilitating transfer of the medication from a first receptacle to a second receptacle.

The medication container can be a fluid tubing set having a Luer fitting on the tip portion such that the at least one optical identifier is applied to the Luer fitting.

The medication device can be a medication administration device including: a housing, a medication port accessible via an outer surface of the housing, an identification sensor disposed within the housing to generate information characterizing contents of the medication container when the fluid outlet of the medication container is being fluidically coupled or is fluidically coupled to the medication port, and a transmitter disposed within the housing and in communication with the identification sensor to transmit the information generated by the identification sensor to a remote data collection system.

The data encapsulated by the at least one optical identifier can include a reference to data accessible via a communications network. The reference to data accessible via a communications network can include, for example, a Uniform Resource Locator, a pointer to a look-up table, a database path, or a file path. The medication device further comprises a memory storing data corresponding to the encapsulated data which is accessed when the medication administration device reads the at least one identifier. The data encapsulated by the at least one optical identifier can be formatted using an industry standard representation of the medication being characterized or a proprietary representation of the medication being characterized. The encapsulated data and/or referenced data accessible via a communications network can include one or more of: an RxNorm identification code, an NDC code (National Drug Code), a segment of the NDC code identifying the drug product, a segment of the NDC code identifying the drug package, a unique identifier code, a human readable alphanumeric, a machine readable code, a name of the medication, a manufacturer of the medication, a re-packager of the medication, a distributor of the medication, a strength of the medication, a dosage form of the medication, dose instructions for the medication, administration instructions for a specific patient, medication formulation, medication package form, medication package size, medication contained volume, medication package serial number, medication lot number, and medication expiration date.

The at least one optical identifier comprises a label applied to the medication container and/or a coded disc, or coded ring secured to the medication container.

The medication container can be bundled with at least one other item bearing a second identifier corresponding to the identifier. Thereafter, after bundling (or in some cases de-bundling), it can be verified that the at least one optical identifier on the medication container corresponds to the second identifier on the at least one other item.

Data (e.g., fourth data) can be received from a medication source characterizing medication contained by the medication source. Such data can be used to generate the at least one optical identifier.

Various verification techniques can be used to verify that the medication within the container matches the data encapsulated in the at least one optical identifier. For example, data can be read from a medication source and compared with the data encapsulated by the at least one optical identifier. In addition or in the alternative, the verification can comprise analytically determining a composition of medication contained within the medication container with actual measurements. This analytically determined composition of medication can be compared with the data encapsulated by the at least one optical identifier. Various analytical technique can be used including, but not limited to: spectroscopy, photometric analysis, electrometric analysis, chromatography, high performance liquid chromatography, mass spectroscopy, physical property measurements, and parametric analysis. Similarly, an analytical determination can be used to generate the at least one optical identifier (as opposed to verifying the contents of the medication container).

At least two redundant optical identifiers can be applied to the medication container. In some variations, all of the redundant optical identifiers are placed within the tip portion to facilitate an accurate reading during rotationally coupling with the medication device. In other cases, at least one of the optical identifiers is placed elsewhere on the medication container so that it can be read differently and/or by different sensing devices (i.e., devices other than the medication device) for various purposes including verification.

The application of the at least one optical identifier can require that a writer device rotate around the medication container when applying the at least one optical identifier. In some variations, only the medication container rotates while in other variations both the writer device and the medication container can rotate. One or more aspect of the application can be human implemented, while in other implementations the application is fully automatic.

The medication container can include a Luer fitting with threads at the tip portion such that one or more of the at least one optical identifier is aligned with a thread engagement of the Luer fitting.

Order data can be received from a computerized physician order entry (CPOE) system or pharmacy information system (PIS). The first data and/or at least one optical identifier can be generated using such received order data.

User-generated input can be received via a graphical user interface that characterizes the medication contained within the medication container. Such input can be used to generate the first data and/or the at least one optical identifier.

In an interrelated aspect, data can be generated or received that includes at least one optical identifier that encapsulates data characterizing at least one medication. Thereafter, the at least one optical identifier is applied to the outer surface of a tip portion of a medication container such that the at least one identifier is positioned to be automatically read by at least one optical sensor of a medication device along the outer surface of the tip portion upon a triggering event. The triggering event can include, for example, fluidically coupling the medication container to the medication device, a pre-defined offset after fluidically coupling the medication container to the medication device, activation of a coupling switch on the medication device, and sensing of fluid flow by the medication device.

In an interrelated aspect, an apparatus for applying at least one optical identifier to a medication container that includes a fluid conduit leading to a fluid outlet and an identification surface at least partially surrounding the fluid conduit and adjacent to the fluid outlet includes: a receiving portion configured to receive the identification surface, and an applicator to apply the at least one identifier to the application surface whereby the identifier at least partially surrounds the fluid outlet.

The applicator can place the at least one optical identifier such that an optical sensor of a medication device can automatically read the at least one optical identifier when the medication container is rotatably mated with medication device.

The identification surface can be a circular cylinder-shaped outer surface that surrounds the fluid conduit. The identification surface can be a polygonal cylinder-shaped outer surface that surrounds the fluid conduit. The receiving portion can be configured to rotatably receive the identification surface. The applicator can be configured to wrap and adhere the at least one optical identifier to the identification surface.

The receiving portion can be a cap within which the identification surface is received and the applicator is configured to apply the at least one optical identifier to the application surface as the identification surface is received within the cap.

The applicator can include an array of applicators that encode the at least one optical identifier onto the identification surface. The applicator can be any more of a laser, an inkjet printhead, a pad printer, a heater element, a laser etcher, and a label placer.

The medication container can include a cylindrical barrel having a surface facing radially inward having radially inward facing Luer lock threads, and an external surface of the cylindrical barrel facing radially outward includes the identification surface. The external surface of the cylindrical barrel can include a distal portion that distally extends beyond the identification surface.

In a further interrelated aspect, a medication is provided that includes a fluid conduit for delivering medication in a direction generally from a proximal portion of the medication container to a distal fluid outlet of the medication container. The medication container defines an identification surface located at a generally distal portion of the medication container and at least partially surrounding the fluid conduit. Thereafter, the identification surface is received into the receiving portion of an encoding apparatus and the optical identifier is applied to the identification surface.

The identification surface can be facing radially outwardly from the conduit so that applying the identifier includes wrapping and adhering a label with the identifier onto the identification surface. Applying the identifier can include wrapping and adhering a label with the identifier onto the identification surface. Applying the identifier can include using a writing system to write the identifier radially inwardly onto the identification surface. The encoding apparatus can comprise a removable cap that is placed over the identification surface in order to apply the identifier. The medication container can include a distally extending portion adjacent to the fluid outlet while surrounding a portion of the fluid conduit, the distally extending portion defines an inside surface having Luer threads extending radially inwardly and an outside surface defining the identification surface which faces radially outwardly from the distally extending portion. The optical identifier can be applied to the identification surface whereby an optical sensor of a medication device can automatically read the identifier when the distal portion of the medication container is rotatably mated with medication device.

In a further interrelated aspect, an apparatus is provided that comprises means for generating or receiving first data comprising an optical identifier, the optical identifier encapsulating second data characterizing at least one medication, and means for applying the at least one optical identifier to the outer surface of a tip portion of a medication container, the at least one identifier being positioned such that it is automatically read by at least one optical sensor of a medication device along the outer surface of the tip portion when the medication container rotatably mates with a complementary fitting on the medication device. Optionally included are means for verifying contents of the medication container after application of the at least one optical identifier.

In still a further interrelated aspect, an apparatus comprises: at least one data processor, memory for storing instructions for execution by the at least one data processor, a write module, and a reader module. The writer module applies at least one first optical identifier to a medication container with the at least one optical identifier encapsulating first data characterizing medication within the medication container. The reader module is coupled to the writer module to confirm, using at least one second optical identifier encapsulating second data characterizing medication within the medication container, whether the first data matches the second data. In some variations, the at least one second optical identifier is applied to the medication container.

In a further interrelated aspect, data characterizing medication within a medication container is received. Thereafter, an identifier encapsulating data characterizing the medication is generated and applied to the medication container. The identifier can be positioned such that it is automatically readable by a medication administration device when the medication is administered to a patient and/or by a medication disposal device when the medication is wasted.

The medication container can take a variety of forms. The medication container can be a syringe comprising a barrel portion and a tip portion comprising a fluid outlet such that the identifier is applied to the tip portion. The tip portion can comprise a cylindrical or conical outer surface terminating at the fluid outlet such that the identifier is applied to the outer surface. The tip portion can comprise a Luer lock fitting such that identifier is positioned on the Luer lock fitting.

The medication container can be a vial having a stopper or a corresponding stopper closure to which the identifier is applied. The medication container can be a medication bag containing a medication solution having a Luer fitting and/or a spikeable port to which the identifier is applied. The medication container can be an envelope having a Luer fitting or a tubing set extending therefrom to which the identifier is applied. The medication container can comprise a fluid transfer device for transferring the medication from a first receptacle to a second receptacle. The medication container can comprise packaging including a medication receptacle containing the medication. The medication container can be a fluid tubing set having a fluid outlet such as a Luer fitting to which the identifier is applied.

The medication administration device can take a variety of forms. For example, the medication administration device can comprise: a housing, a medication port accessible via an outer surface of the housing, an identification sensor disposed within the housing to generate information indicative of contents of the medication container when the fluid outlet of the medication container is fluidically coupled to the medication port, and a transmitter disposed within the housing and in communication with the identification sensor to transmit the information generated by the identification sensor to a remote data collection system.

The encapsulated data can comprise a reference to data accessible via a communications network. In such cases, the encapsulated data can include a Uniform Resource Locator, a database path, a pointer to a look-up table, or a file path such that the medication administration device accesses such remote information (which can be used, for example, for more informed patient treatment, etc.). In addition or in the alternative, the medication administration device can comprises a memory storing data corresponding to the encapsulated data which is accessed when the medication administration device reads the identifier.

The encapsulated data can be formatted using an industry standard representation of the medication being characterized or a proprietary representation of the medication being characterized. The referenced data accessible via a communications network can include one or more of: an NDC code (National Drug Code), a segment of the NDC code identifying the drug product, a segment of the NDC code identifying the drug package, a unique identifier code, a human readable alphanumeric, a machine readable code, a name of the medication (using any drug naming convention, including but not limited to, generic names, trade names, and normalized drug naming system representations (e.g.

RxNorm)), a manufacturer of the medication, a re-packager of the medication, a distributor of the medication, a strength of the medication, a dosage form of the medication, dose instructions for the medication, administration instructions for a specific patient, medication formulation, medication package form, medication package size, medication contained volume, medication package serial number, medication lot number, and medication expiration date. The encapsulated data can additionally or alternatively also include such information.

The identifier can take a variety of forms. For example, the identifier can be any of: optical identifiers, magnetic identifiers, RFID identifiers, and mechanically encoded identifiers. The identifier can be etched on an outer surface of the medication container. The identifier can be a mechanical element secured to or extending from the medication container. The identifier can include a coded disc or coded ring secured to the medication container.

The medication container can be bundled with at least one other item (e.g., second medication container, fluid adapter, tubing set, packaging, etc.) bearing a second identifier corresponding to the identifier. In such cases, it can be verified, after the bundling, that the identifier on the medication container corresponds to the second identifier on the at least one other item.

In a further aspect, data is read from a medication source characterizing medication contained by the medication source. Thereafter, an identifier encapsulating data characterizing the medication is generated and is applied to a medication container filled or to be filled with the medication from the medication source. The identifier can be positioned such that it is readable by a medication administration device when administering the medication to a patient or when disposing the medication without deliberate effort on behalf of a clinician to facilitate information transfer between the medication container and the medication administration device or the medication wasting device.

In a further aspect, a medication identification encoding and verification apparatus is provided that includes a medication information source, an identification information reader (ID reader), an identification information writer (ID writer), a verification method to check the read information and a medication identification target (ID target). The ID reader includes a detector, scanner or imaging element to receive the medication identification information. The ID writer includes a marking element to deposit or encode identification information onto the ID target. The ID target receives the encoded identification information mark, image, code or other information rich media content. If the medication container is a syringe, the encoded information on the target is positioned such that it can be read by a medication administration device when administering the medication to a patient without deliberate effort on behalf of a clinician to facilitate information transfer between the medication container and the medication administration device.

In another aspect, a medication identification encoding and verification apparatus is provided with a second ID reader, a verification comparator, an identification information verification writer (IDV writer) and a second identification information target on packaging materials. The second ID reader includes a scanner element to receive medication information from a medication container or associated medical packaging. The verification comparator includes means for comparing desired identification information to medication container identification information. The IDV writer includes a marking element to deposit or encode identification information on a second ID target. The second ID target receives the second identification information mark. The second ID target can be packaging material.

A read-write instrument can be provided for reading a medication identification code source and writing information to a target for encoding the target with the medication identification information used, for example, in a pharmaceutical manufacturing facility. In a further variation that can be used in a pharmaceutical repacking operation or in-hospital pharmacy, the reader can identify medication information from a multi-dose container and the writer can then encode single or partial dose information on the target. In this variation, the written information can be different from the original read information in that it can indicate smaller volumes, lower concentrations or be a patient specific dose. Multiple writes can be made on multiple targets to encode information about aliquots of medication written onto multiple single dose containers.

The information reader aspect of the read-write instrument can be any one of a linear barcode reader, a 2D barcode reader, a magnetic strip reader, an image capture device, a camera, a manual data input information string, a stored alpha numeric character string, a unique symbolic identifier.

The information writer aspect of the read-write instrument can be any one of a laser, a printer, a hot stamp, a magnetic coding element, an electronic coding element, an RFID writer, a printed label, a coded disc, or coded ring element to be affixed to a medication container or packaging.

The information target can be any one of a syringe including but not limited to an empty and/or a prefilled syringe, a bag, a vial, a medication transfer apparatus including but not limited to a fluid administration set, a vial transfer apparatus, packaging, a medication container ID label marking element or coded disc, or coded ring to be affixed to the medication container. The information element can be applied to the tip portion (i.e., the portion of the medication container having the fluid outlet and a diameter smaller than or equal to the chamber of the medication container, etc.) or fluid outlet of the medication container.

The medication container and or the vial transfer apparatus can be enveloped in a sterile pouch (i.e., enclosure, etc.). The sterile pouch can contain information indicative of the encoded information on the information transfer element. The medication information transfer element can be part of a kit that also contains the vial and medication instructions for use. The kit can be manufactured complete by a pharmaceutical company including the medication in the vial and the information transfer apparatus. The kit can be packaged by a local pharmacy, a pharmaceutical repackaging operation or an in-hospital pharmacy and can include a pharmaceutical company packaged vial and the information applied to a fluid transfer apparatus.

In the pharmacy and/or pharmaceutical repackaging kit configuration the pharmacy can match and verify the medication information on the vial and vial packaging with the medication information on the transfer apparatus packaging and the information transfer element. The encoded information on the transfer apparatus can be positioned such that it can be read by a medication administration device when administering the medication to a patient without deliberate effort on behalf of a clinician to facilitate information transfer between the medication container and the medication administration device. Once matched and verified the pharmacy can join the vial and information transfer apparatus into a secondary package and label the kit. The secondary package can provide a tamper evident element providing assurance of maintaining the matched elements.

The secondary package can contain pharmacy specific information including lot number, packaging date, medication expiration date, dosage, patient information and/or container serial number.

In a pharmacy and/or pharmaceutical repackaging operation, the read-write instrument can be provided for reading a medication identification code source and writing information to multiple targets with the medication identification information encoded on multiple medication containers. In this variation, a multi-dose medication container (vial, Act-O-Vial™, bag, bottle, ampoule, syringe, etc.) is provided to the pharmaceutical filler. Using the method, the pharmaceutical filler can encode multiple containers, or transfer elements, sub-dividing the contents of a multi-dose container into more than one dose administration sub-container. The multi-dose container information can be read and verified with an identification code. Then multiple sub-containers can be written (encoded) with sub-container information. The written sub-container information can contain the same or different information than the multi-dose medication container. The sub-container information can include any information useful for characterizing the contents of the sub-container (such as the data described above). If the sub-container is a syringe, the encoded information on the target can be positioned such that it can be read by a medication administration device when administering the medication to a patient without deliberate effort on behalf of a clinician to facilitate information transfer between the medication container and the medication administration device.

The encoded information can be selected from a group comprising: optically encoded information, optical image information, magnetically encoded information, radio frequency detectable information, and mechanically detectable information. The encoded information can include a unique identifier, NDC information, dose, concentration, package serial number, lot number, expiration date. The encoded information can be based on an industry standard representation of information content or a proprietary representation of the content.

Computer program products are also described that comprise non-transitory computer readable media storing instructions, which when executed one or more data processor of one or more computing systems, causes at least one data processor to perform operations herein. Similarly, computer systems are also described that may include one or more data processors and a memory coupled to the one or more data processors. The memory may temporarily or permanently store instructions that cause at least one processor to perform one or more of the operations described herein. In addition, methods can be implemented by one or more data processors either within a single computing system or distributed among two or more computing systems.

The current subject matter provides many advantages. For example, by allowing for the automatic identification of the contents of medication containers (whether during administration of such medication or as part of a verification process during manufacture/preparation), medication administration errors can be greatly reduced. In addition, adverse effects from drug allergies and incompatible medications can be significantly minimized by providing a medication container that can be automatically identified. Providing a medication container labeled in a way that is automatically readable by a medication administration device without deliberate effort on the part of the clinician, greatly reduces the possibility of human error or that the label identification step will be skipped or adversely abbreviated in an effort to focus on immediate patient care needs. Lastly, proper record keeping can be maintained with regard to wasted medication (which is especially important with regard to controlled substances).

The details of one or more variations of the subject matter described herein are set forth in the accompanying drawings and the description below. Other features and advantages of the subject matter described herein will be apparent from the description and drawings, and from the claims.

DESCRIPTION OF THE DRAWINGS

The accompanying drawings, which are incorporated in and constitute a part of this specification, show certain aspects of the subject matter disclosed herein and, together with the description, help explain some of the principles associated with the disclosed embodiments. In the drawings.

Like reference symbols in the various drawings indicate like or similar elements.

DETAILED DESCRIPTION

Figure 1A:
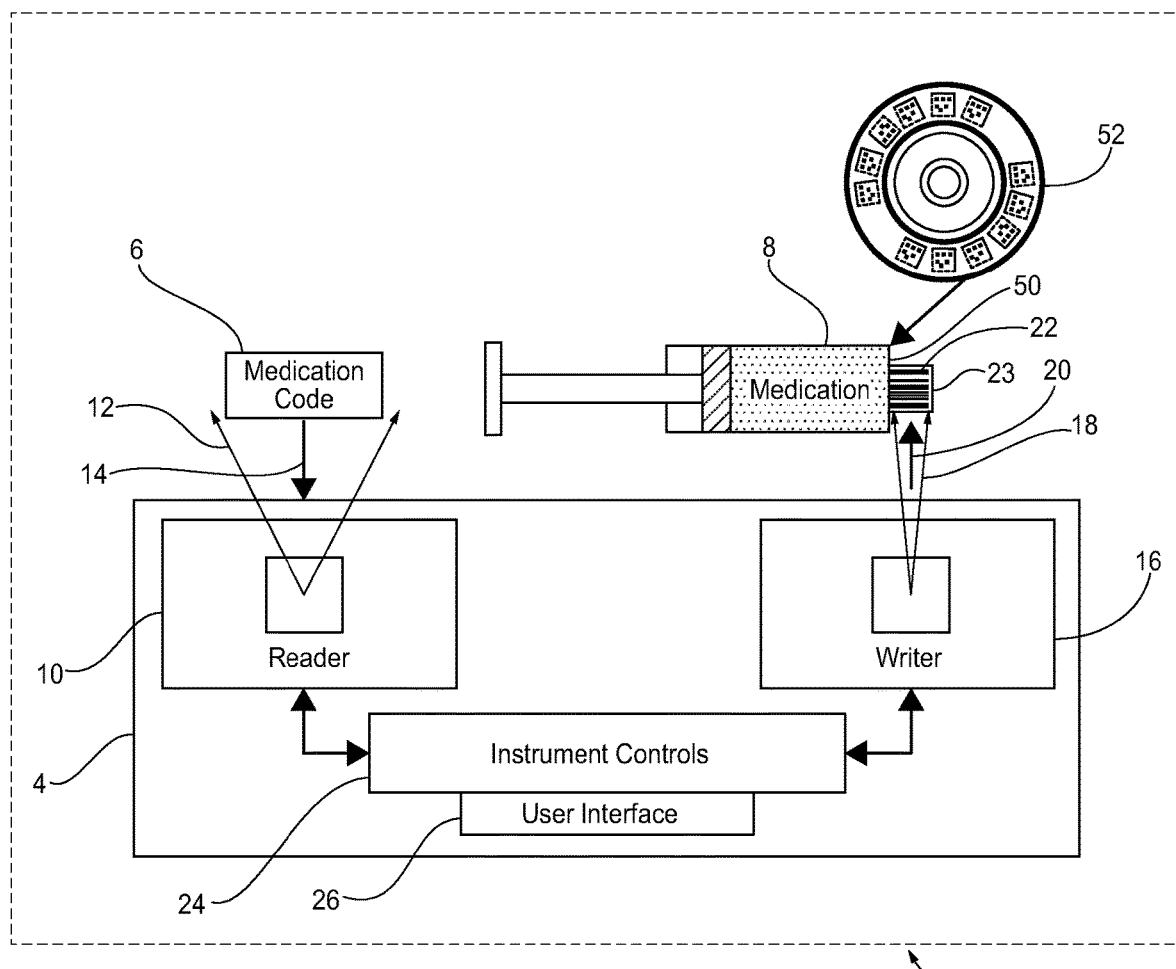
FIG. 1A is a diagram illustrating a medication identification information read and write apparatus for use with a syringe container.

FIG. 1A is a diagram illustrating a medication identification information read and write apparatus 2 that can be used to implement a medication container encoding and identification method. Apparatus 2 can include a read-write instrument 4 that can include one or more information readers 10, an information writer 16 and an information target 8. With such an arrangement or device, an entity such as a pharmaceutical manufacturer, a pharmaceutical repackager, a local pharmacy or an in-hospital pharmacy can access or read medication identification information 14 from medication code source 6. This read medication identification information 14 can be subsequently written, applied (e.g., deposited, encoded, etc.) in the form of medication identification information 20 onto or into information target 8 for the purpose of encoding target 8 at the fluid outlet. The encoded medication identification information on the target (sometimes referred to herein as an "identifier") can be positioned such that it can be read by a medication device 114 (described later) when administering the medication to a patient without deliberate effort on behalf of a clinician to facilitate information transfer between the medication container 8 and the medication device 114. This is further described below in connection with FIG. 10. As used herein, unless otherwise stated, a medication device 114 can comprise one or more of a medication administration device for administering medication from a medication container to a patient or a medication wasting device for disposal of unused medication within a medication container. In some cases, delivery of a fluid contained within the medication container to the medication device can be manually activated by a caregiver.

The medication identification information 20 can be displayed on a variety of locations on an information target 8 (i.e., a medication container, etc.). For example, when the information target 8 is a syringe, the medication identification information 20 can be positioned on the tip of the syringe. More specifically, in some implementations, the medication identification information 20 can be placed on a tapered portion of the tip, a Luer lock fitting on the tip, and a portion of the tip interposed between the tapered portion and the cylindrical chamber of the syringe.

The current subject matter is applicable to a wide variety of medication containers. Examples of medication containers include: a pre-filled or empty needle-less syringe having a fluid outlet at a tip of the syringe, a vial having a fluid outlet corresponding to the stopper at the vial closure, a bag containing a premixed solution having a Luer fitting connector or an IV set spikeable port, an envelope (e.g., disposable, rigid, semi-rigid or flexible envelope, etc.) having an integral Luer fitting on tubing extended therefrom, a fluid transfer device used with medication vials having a Luer fitting connector, and/or a fluid delivery tubing set having an integral Luer fitting at one end of the tubing.

The medication code source 6 can be/include any one or more of a barcode (one or two dimensional), an optical image (e.g. picture, symbol, image, hologram, etc.), an RxNorm identification code, an NDC code (National Drug Code), a segment of the NDC code identifying the drug product, a segment of the NDC code identifying the drug package, a unique identifier code, human readable code, a machine readable code, a manually entered code or other codes that can be created to uniquely identify one or more of a medication's name (using any drug naming convention, including but not limited to, generic names, trade names, and normalized drug naming system representations (e.g. RxNorm)), manufacturer, re-packager, distributor, strength (concentration), dosage form, dose instructions (whether generic for all patients or specifically prescribed for a particular patient), formulation, package form, package size, contained volume, package serial number, lot number, expiration date.

Additional complementary information can also be included within the medication code source 6 such as a reference to a hospital formulary or drug vocabulary database such as those offered by First Databank, Multum, and MediSpan (via, for example, a URL, etc.) which can include additional information regarding the medication such as how it interacts with other medications and/or information regarding medications that are often administered along with the specified medication. As an example, before and/or coincident to the medication being administered, such complementary information may be accessed by a reader (whether at the point of administration or otherwise) so that additional information can be presented regarding the medication (including which medications should not be administered concurrently). In addition, in some implementations, it can be determined whether there is a possibility of an adverse reaction if the medication is delivered (whether via overmedication or interaction with previously delivered medications or due to some potential patient adverse condition). Such complementary information can also identify other medications that are often administered with the identified medication (especially in the case of complex protocols).

During use, the operator of read-write instrument 4 first determines which medication code source 6 is to be used and positions it in range of reader 10. Alternately, the operator can manually enter medication code source 6 information by using user interface 26. Secondly, the operator positions target 8 in range of writer 16. This positioning of target 8 may be a manual process or facilitated by automated equipment. The scanner element 12 of the reader 10 reads medication code source 6 and produces read information 14. Instrument control 24 receives read information 14 and prepares for a writing operation. Writer 16 receives read information 14 from instrument control 24 and writing element 18 of the writer 16 produces written information 20 to be written or deposited on target 8's fluid outlet 23. Writing element 18 can be one of a laser writer, a hot stamp, a printer, an ink-jet printer, a thermal printer, a thermal transfer printer, a pad printer, a screen printer, an engraver, a photo engraver, an etcher, a magnetic encoder, an electronic data packet message, or a surface treatment facilitating optical, magnetic, electronic, mechanical or proximity recognition. The identifier 22 can be applied manually, automatically or semi-automatically. Identifier 22 can be visible by a human, ultraviolet visible, infrared visible or RF visible. The medication device 114 can include a detection sensor 124 (described later). The detection sensor can be an optical sensor, an ultraviolet sensor, a magnetic sensor, a mechanical sensor, a proximity sensor, or a capacitive sensor. Identifier 22 can be tamper evident such that if removal is attempted identifier 22 is destroyed or rendered unreadable by the medication device 114. Once written, target 8 is encoded with information from medication code source 6.

As a first alternative, the writer 16 can deposit the encoded information on an adhesive backed element which can then be applied to target 8 (e.g., an RFID tag or other machine readable label applied to target). As a second alternative, writer 16 may apply a coded article such as a coded ring or collar to target 8. As a third alternative the coded information or article can be radially written on the syringe surface 50 or take the form of coded disc 52 applied to surface 50.

Figure 1B:
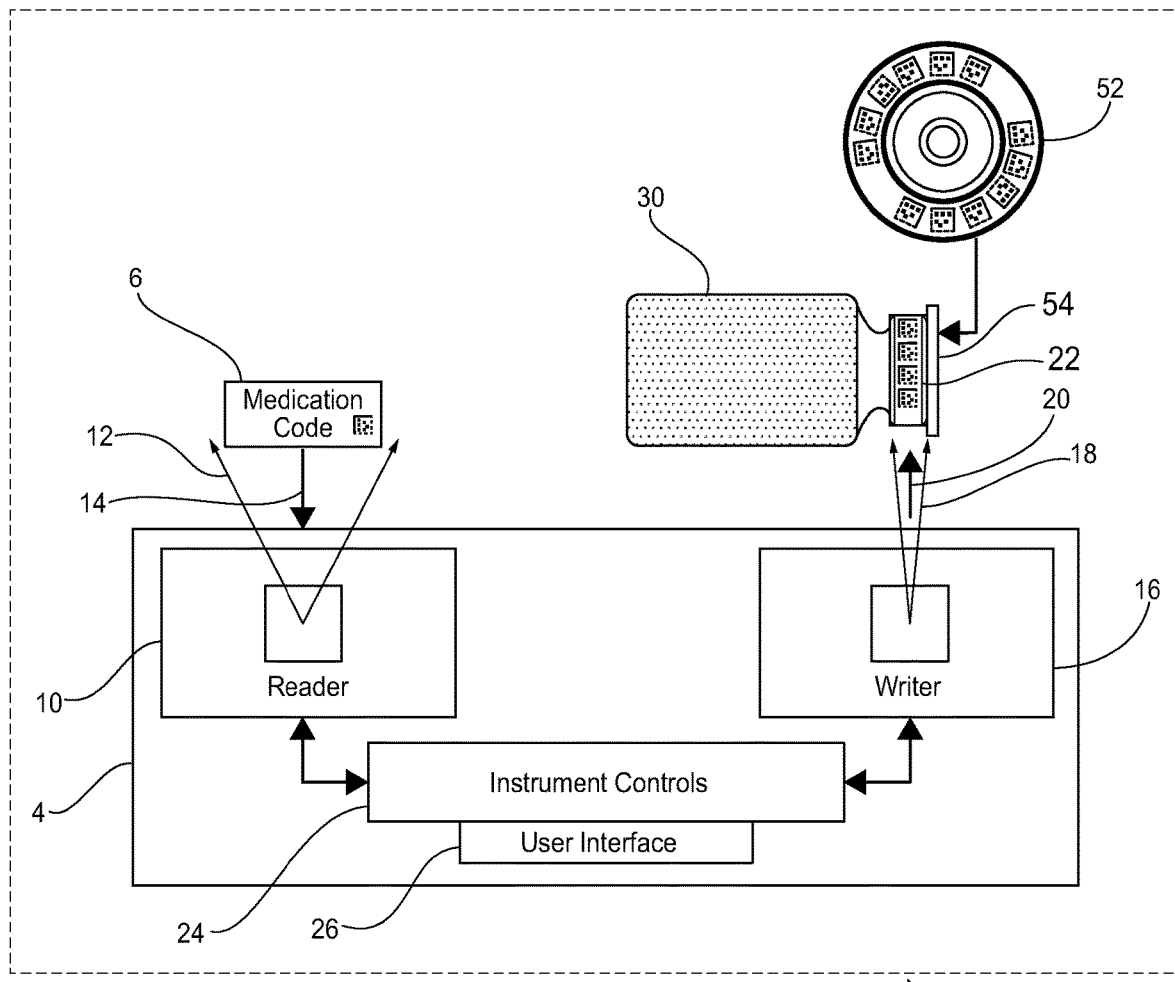
FIG. 1B is a diagram illustrating a medication identification information read and write apparatus for use with a vial container.

FIG. 1B is a diagram illustrating a medication identification information read and write apparatus 2 for use with a vial. Similar to FIG. 1A, apparatus 2 can include a read-write instrument 4 that can include one or more information readers 10, an information writer 16 and an information target 30. With such an arrangement, an entity or device such as a pharmaceutical manufacturer, local pharmacy or in-hospital pharmacy can access or read medication identification information 14 from medication code source 6. This read medication identification information 14 can be subsequently written, deposited or encoded in the form of medication identification information 20 onto or into information target 30 for the purpose of encoding target 30 at the fluid outlet (vial septum, stopper or stopper closure).

Similar to FIG. 1A, additional complementary information can also be included within the medication code source 6 such as a reference to a database or document (via, for example, a URL, etc.) which can include additional information regarding the medication such as how it interacts with other medications and/or information regarding medications that are often administered along with the specified medication.

As a first alternative, the writer 16 can deposit the encoded information on an adhesive backed element which can then be applied to target 30 (e.g., an RFID tag or other machine readable label applied to target). As a second alternative, writer 16 may apply a coded article such as a coded disk 52 to target 30. As a third alternative the coded information or article can be radially written on the vial surface 54 in a pattern similar to disc 52.

Figure 2:
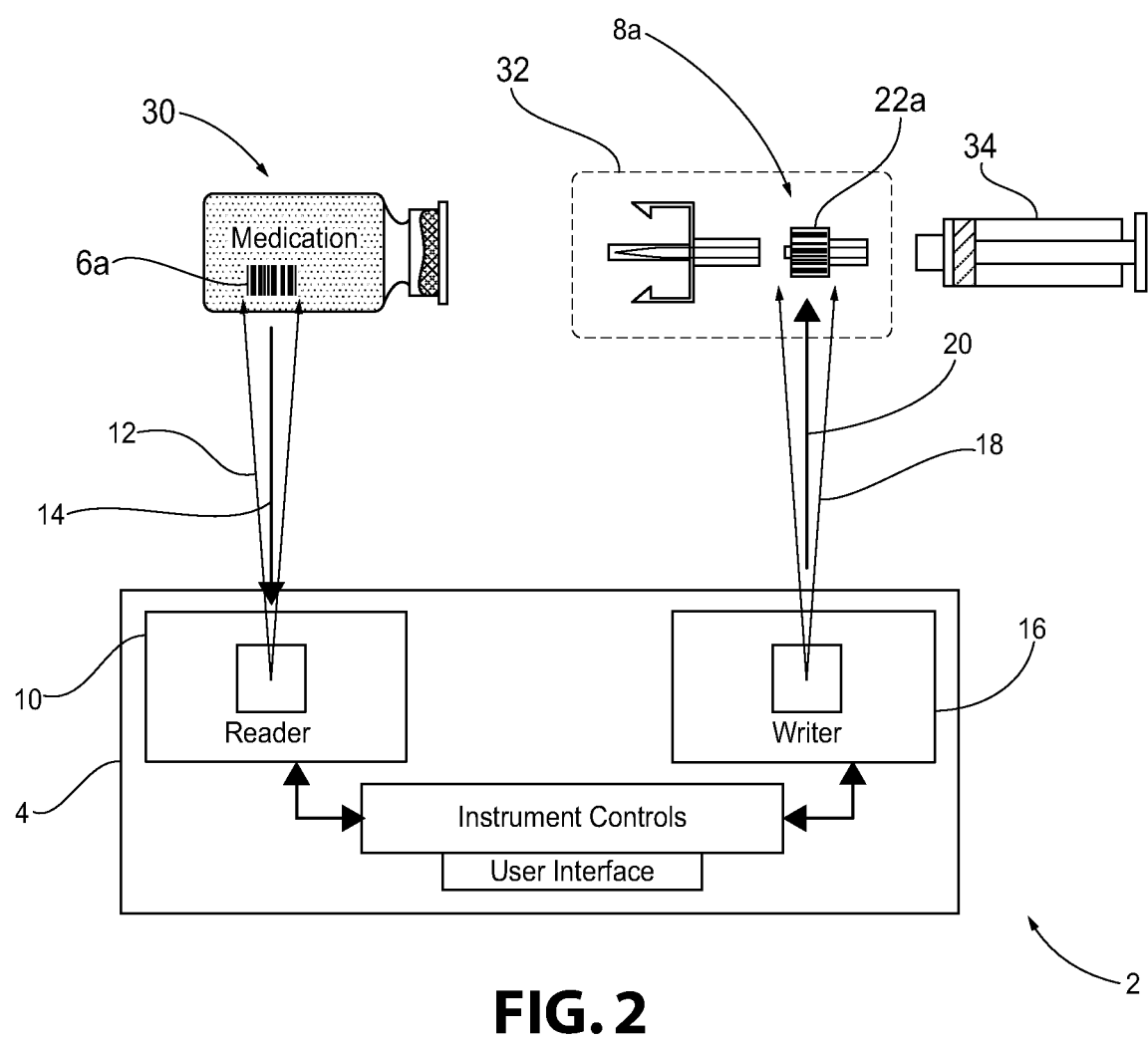
FIG. 2 is a diagram illustrating an alternate medication identification information read and write apparatus of FIG. 1.

FIG. 2 is a diagram illustrating an alternative medication identification information read and write apparatus. In this variation, the scanner element 12 of reader 10 reads medication code source 6a from vial 30 and produces read information 14. Instrument control 24 receives read information 14 and prepares for a writing operation. Writer 16 receives read information 14 from instrument control 24 and the writing element 18 of writer 16 produces written information 20 to be written or deposited on target 8a's fluid outlet 23. Writing element 18 can be one of a laser writer, a printer, an ink-jet printer, a thermal printer, a thermal transfer printer, a pad printer, a screen printer, an engraver, a photo engraver, an etcher, a magnetic encoder, an electronic data packet message, a label applicator or application method or a surface treatment facilitating optical, optical image, magnetic, electronic or proximity recognition. Once written, target 8a is encoded with medication code source 6a's information. In this variation, target 8a is part of vial adapter and ID transfer element 32 designed for use with empty container 34 (shown here as a syringe) for the withdrawal and transfer of medication to a patient. As an alternative, the writer can deposit the encoded information on an adhesive backed element which can then be applied to target 8a. As a second alternative, writer 16 may apply a coded article such as a coded plastic ring or coded collar to target 8a.

Other variations of medication containers and information targets can be incorporated that use various forms of medication code source 6a to provide information about the contents of the container and different target 8a with alternate fluid outlet 23 configurations. Targets can be encoded as separate parts and then grouped with other parts as assemblies.

The apparatus and process depicted in FIG. 2 customizes medication vial 30 to improve accuracy and safety of medication delivery. Vial 30 can be customized to be utilized by a self-auditing medication delivery system including a fluid input (not shown) that is coupled to a patient. During medication delivery to a patient, fluid outlet 23 is coupled to container 34 (e.g., a syringe). Fluid outlet 23 can be coupled to a fluid input (not shown) and then medication within container 34 is dispensed through fluid outlet 23 and into the fluid input. The fluid input (not shown) includes a reading device 124 (not shown) that reads encoded information 22 from fluid outlet 23 and can then utilize the information 20 to verify that a type and quantity of medication delivered by container 34 is proper for the patient. Thus, the current subject matter provides an advantageous way of customizing medication containers to enable a verification of proper medication delivery.

In a further implementation, vial 30 can be customized to provide a particular dosage of medication for a patient. Container 34 may be configured to hold a fraction of the entire volume of medication held in medication vial 30 as will be discussed later regarding FIG. 7. Information 20 may include information that is indicative of a dosage to be delivered to the patient from container 34. Such an implementation is advantageous in that it allows customization of medication to enable dosing to a particular patient without error. One example of such customization may be providing a dose for pediatrics or for a patient of a given weight class. In another variation, container 34 may be a "multi-dose" syringe configured to hold multiple doses of medication from vial 30. In yet further variations, medication in container 34 may be diluted and information 20 may additionally be indicative of dilution parameters. In yet further variations, medication in container 34 may be divided into multiple sub-container targets and repackaged by a pharmacy as will be discussed later.

Figure 3:
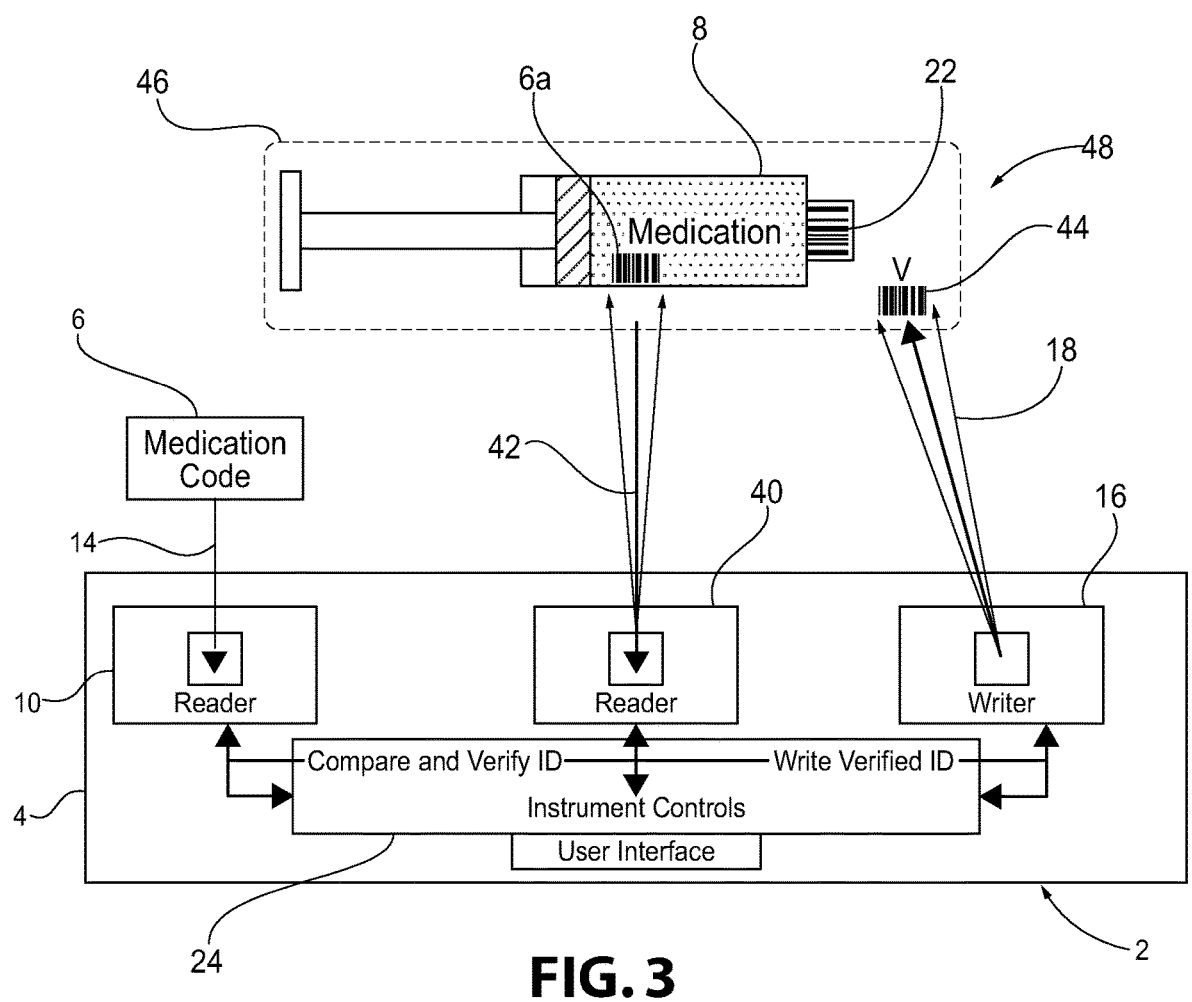
FIG. 3 is a diagram illustrating an identification information read, write and verification apparatus.
Figure 4:
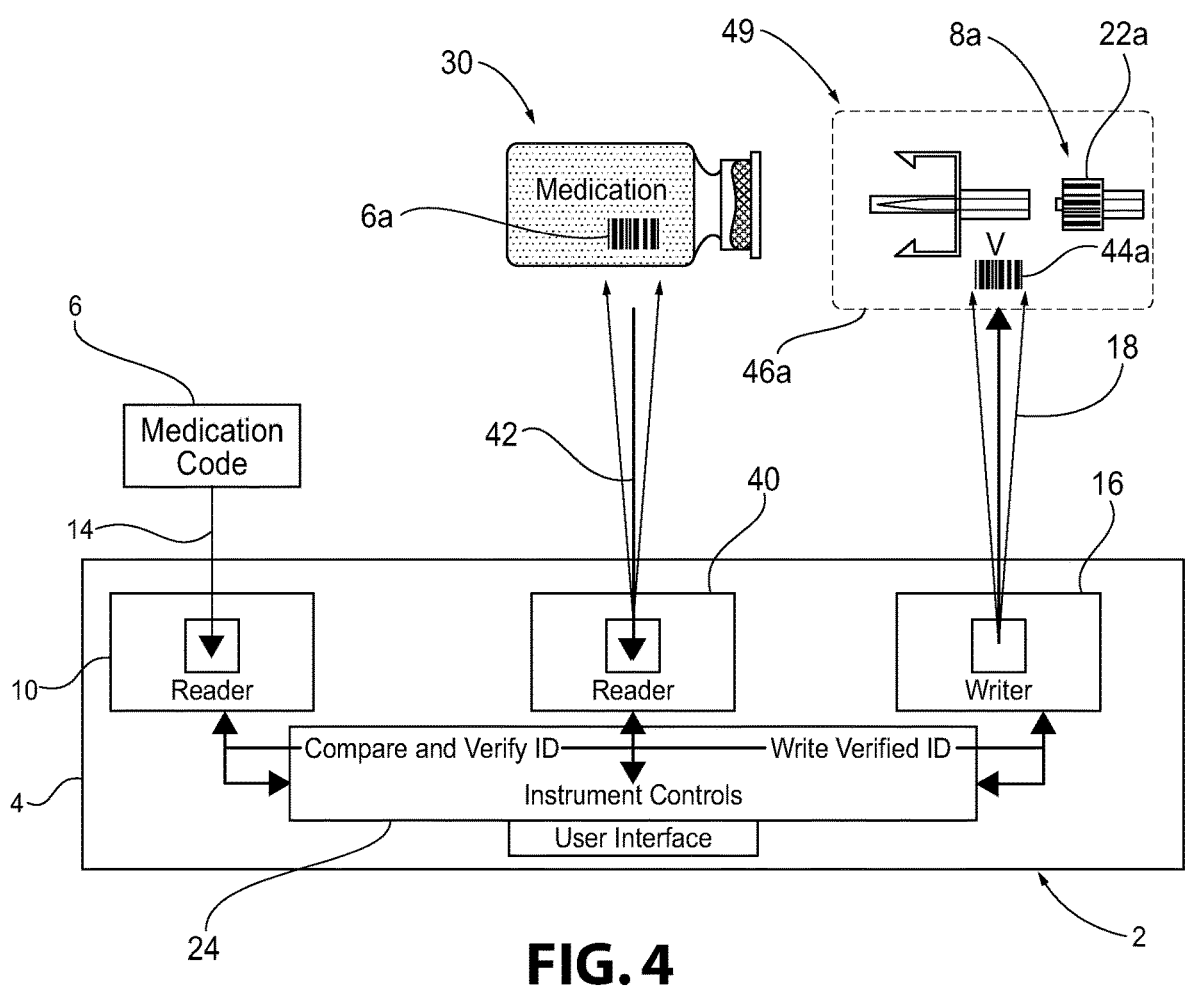
FIG. 4 is a diagram illustrating an alternate identification information read, write and verification apparatus of FIG. 3.
Figure 5:
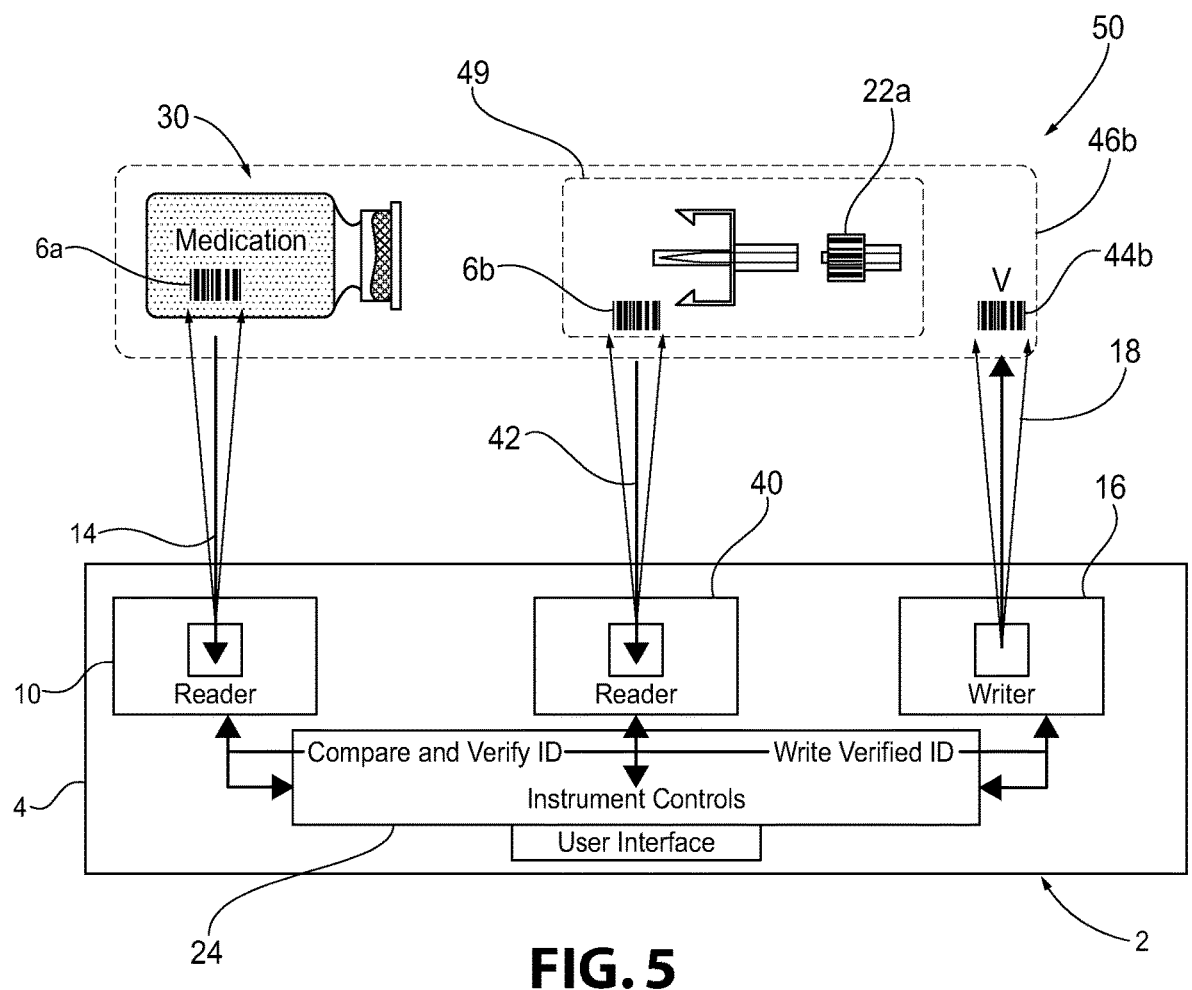
FIG. 5 is a diagram illustrating a second alternate identification information read, write and verification apparatus of FIG. 3.

FIGS. 3, 4 and 5 illustrate arrangements to read encoded medication information from various medication code sources and encoded targets and to verify their identity and write identifying information on packaging. FIG. 3 illustrates a first variation of apparatus 2 wherein the medication container is a prefilled or empty syringe. In this case medication code source 6 is read by reader 10 providing a desired identification. A second reader 40 (or a second read operation/position of first reader 10) can scan medication code source 6a and produces read information 42. Instrument control 24 compares information 14 to information 42 and verifies that their identity matches. Writer 16 receives information 42 from instrument control 24 and writing element 18 writes information 44 onto package 46. A human readable indication of the verification, "V", can be part of written information 44. Package 46 can be a box, envelope, pouch or other medical product packaging forming fully packaged and labeled syringe 48. Alternately, reader 10 can scan medication code 6a instead of medication code 6 and reader 40 can scan encoded information 22 instead of medication code source 6a. Here, instrument control 24 compares medication code 6a to information 22 and verifies identity before writing information 44.

FIG. 4 describes a second variation of apparatus 2 wherein the medication container is vial 30 to be used with vial adapter and transfer apparatus 49. In this case medication code source 6 is read by reader 10 providing a desired identification. A second reader 40 (or a second read operation/position of first reader 10) scans medication code source 6a and produces read information 42. Instrument control 24 compares information 14 to information 42 and verifies their identity. Writer 16 receives information 42 from instrument control 24 and writing element 18 writes information 44a onto package 46a. A human readable indication of the verification, "V", can be part of written information 44a. Package 46a can be a box, envelope, pouch or other medical product packaging forming fully packaged vial adapter and transfer apparatus 49. Alternately, reader 10 can scan medication code 6a instead of medication code 6 and reader 40 can scan encoded information 22a instead of medication code source 6a. Here, instrument control 24 compares medication code 6a to information 22a and verifies identity before writing information 44a.

FIG. 5 is a third variation of apparatus and method 2 wherein the medication container is vial 30 to be used with vial adapter and transfer apparatus 49. In this case medication code source 6a is read by reader 10 providing a desired identification. A second reader 40 (or a second read operation/position of first reader 10) scans medication code source 6b and produces read information 42. Instrument control 24 compares information 14 to information 42 and verifies their identity. Writer 16 receives information 42 from instrument control 24 and writing element 18 writes information 44b onto package 50. A human readable indication of the verification, "V", can be part of written information 44b. Package 50 can be a box, envelope, pouch or other medical product packaging forming fully packaged vial 30 and vial adapter and transfer apparatus 49. Alternately, reader 40 can scan information 22a instead of medication code 6b. Here, instrument control 24 compares medication code 6a to information 22a and verifies identity before writing information 44b.

Figure 6:
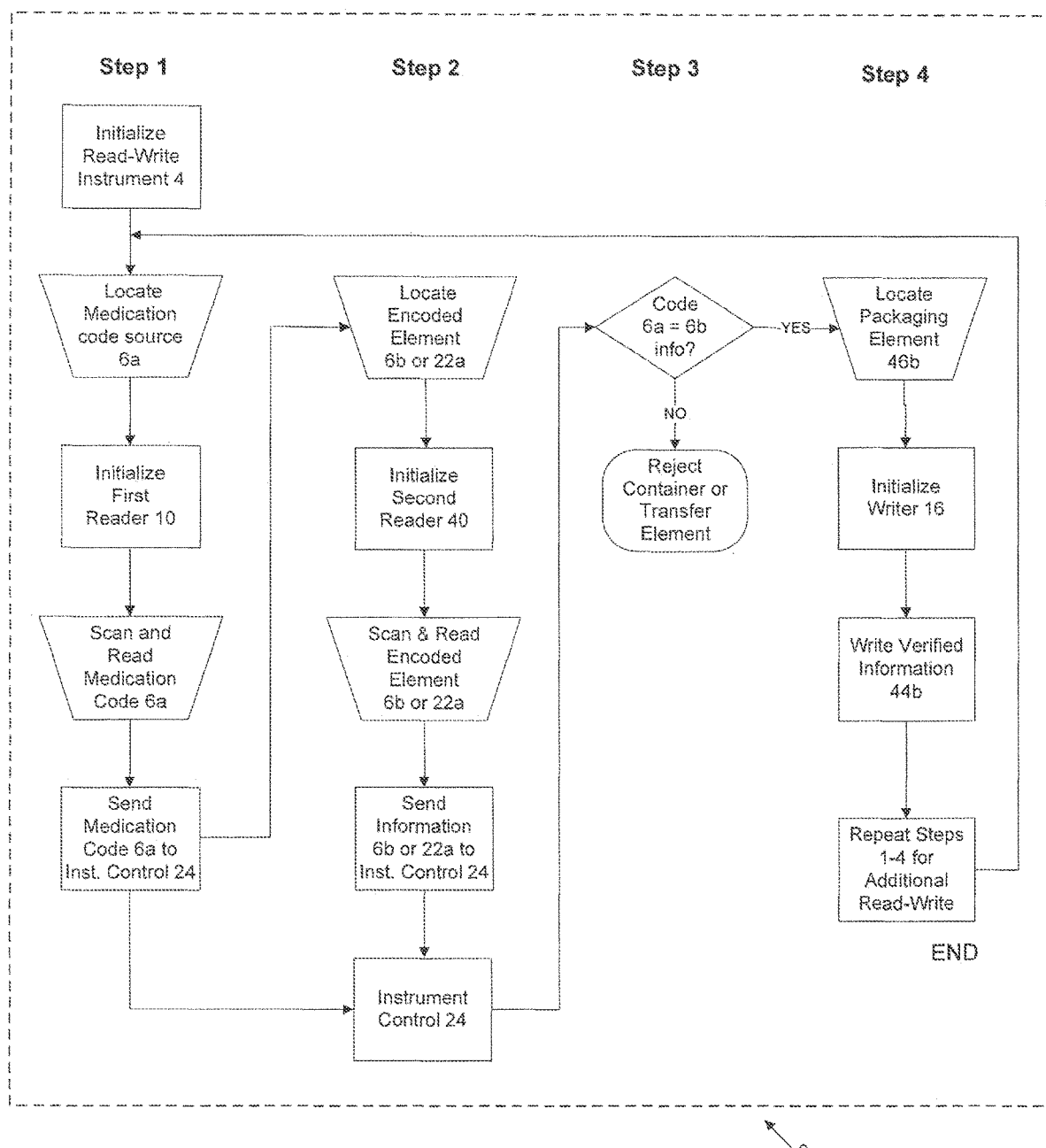
FIG. 6 is a flow diagram illustrating a sequence of steps describing a method and use of an apparatus such as the one in FIG. 5.

FIG. 6 is a process flow diagram relating to the use of a medication identification encoding and verification apparatus 2 such as is shown in FIG. 5.

Step 1—Initialize instrument 4, locate medication code source 6a, initialize first reader 10; locate, scan and read medication code source 6a, and send medication code 6a to instrument control 24.

Step 2—Locate encoded element 6b or 22a, initialize second reader 40, scan and read encoded element, and send information to instrument control 24.

Step 3—Compare first read information (e.g., medication code 6a) to second read information (encoded element 6b or 22a) and verify information identity. Reject container or transfer element if there is not a match.

Step 4—Locate packaging element 46b, initialize writer 16, write verified information 44b, and repeat from step 1 thru step 4 if needed/desired.

Figure 7:
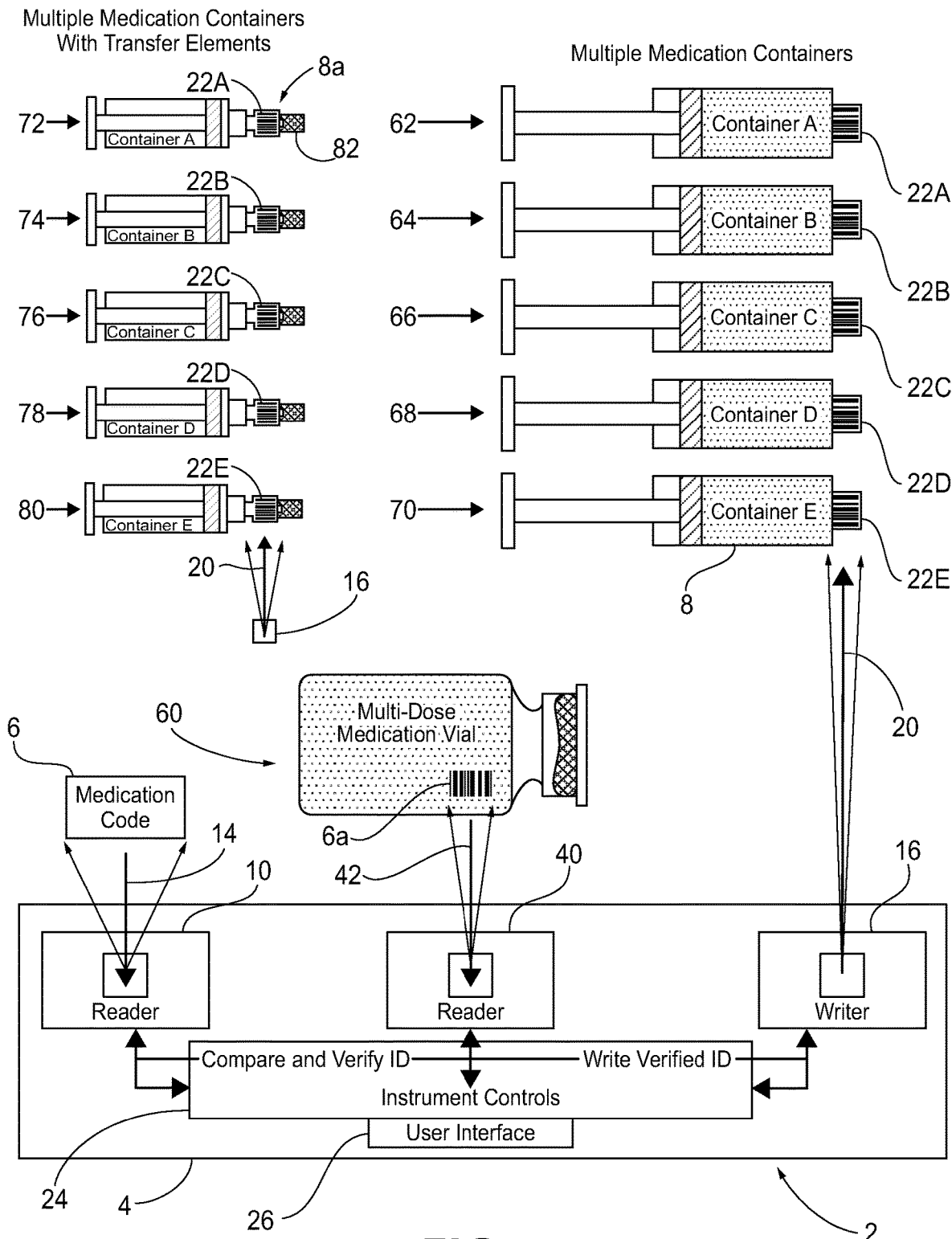
FIG. 7 is a diagram illustrating a third alternate identification information read, write and verification apparatus of FIG. 3.

FIG. 7 is a diagram illustrating a fourth variation medication identification information read-write and verification apparatus and method. This variation can be used in a pharmacy to read information from multi-dose medication container 60 and write information 20 onto multiple medication containers 62, 64, 66, 68, 70 (or onto multiple medication transfer elements 8a with cap 82 and attached to medication containers 72, 74, 76, 78, 80 as shown in the upper left). Encoded information 22A, 22B, 22C, 22D, and 22E can be written multiple times onto multiple containers 62, 64, 66, 68, 70 (or transfer elements 72, 74, 76, 78, 80) respectively. Any number of multiple doses and multiple medication containers can be used; there are five containers (A-E) shown in this example. The written information 20 can be the same for each medication container or it can be different. When different, the pharmacy operator can use user interface 26 to customize information 20 which can contain the same or different dose amounts (dose volume, concentration, etc.), different patient identifiers, different serial numbers, etc. In multi-dose container 60 arrangements, the reader 40 and/or instrument controls 24 can record the amounts introduced into each medication container 62-70 (or 72-80) and/or the amount remaining in the multi-dose medication container 60. This recorded information can be used for pharmacy records.

The method and apparatus of FIG. 7 depicts customization of medication container 60 for dosages that are smaller than the amount of medication held in medication container 60. This customization can provide a convenience to a caregiver and avoids error. A fluid receiving port (not shown here but can be seen in FIG. 10) coupled to a patient includes a reader that is configured to read the information 22 to verify and record a proper dose as being provided to a patient. The method and apparatus depicted in FIG. 7 along with the fluid receiving port connected to a patient and medication container coded fluid outlet reader provides an effective combination of dosage customization and electronic auditing to prevent error and to provide an automated form of electronic record keeping. The encoded information 20 on the target can be positioned such that it can be read by a medication administration device (fluid receiving port) when administering the medication to a patient without deliberate effort or work flow interruption on behalf of a clinician to facilitate information transfer between the medication container and the medication administration device.

Figure 8:
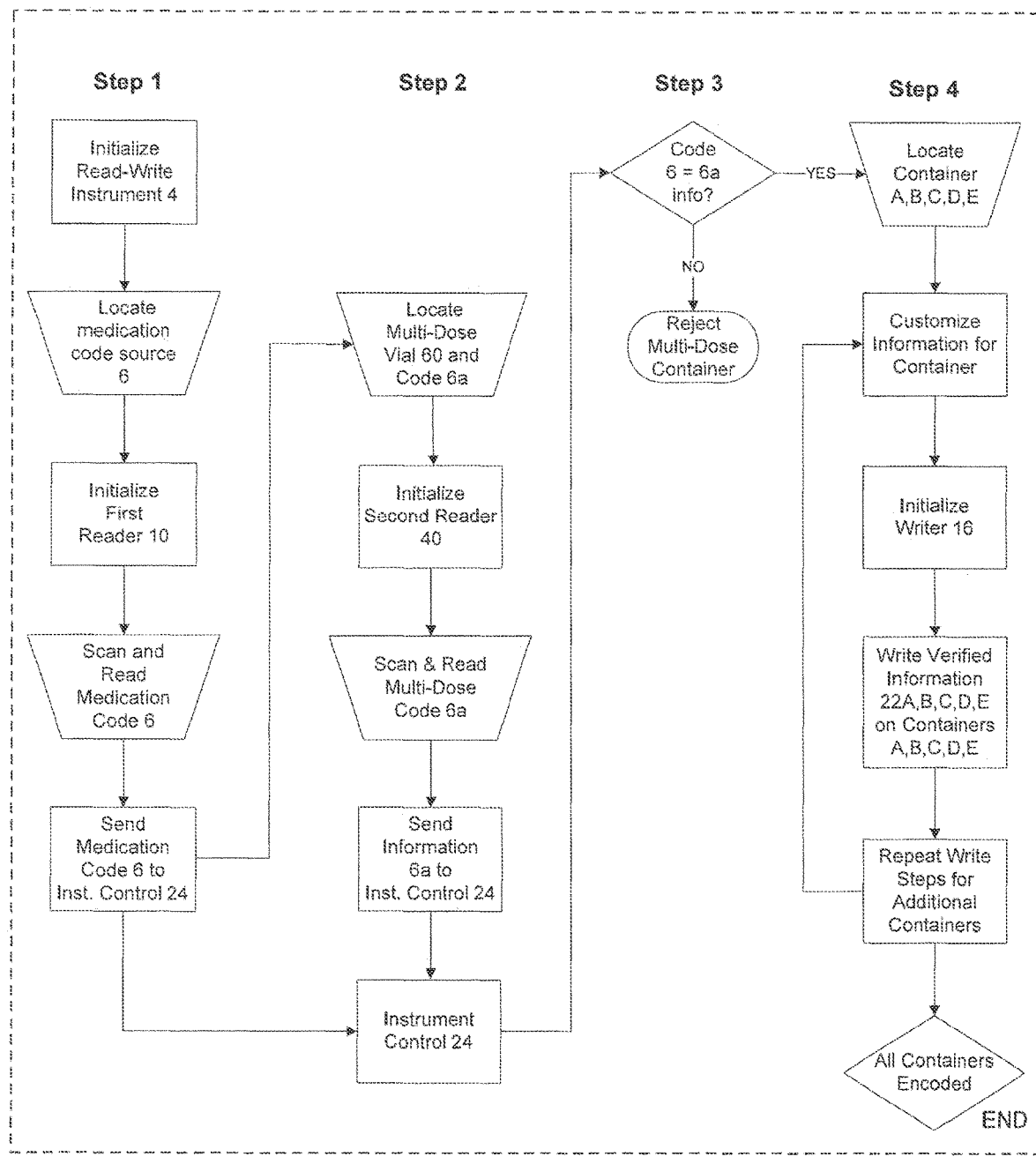
FIG. 8 is a flow diagram illustrating a sequence of steps describing a method and use of an apparatus such as the one in FIG. 7.

FIG. 8 is a process flow diagram relating to the use of a medication identification encoding and verification apparatus 2 such as is shown in FIG. 7.

Step 1—Initialize instrument 4, locate medication code source 6, initialize first reader 10, locate, scan and read medication code source 6, and send medication code 6 to instrument control 24.

Step 2—Locate multi-dose vial 60, initialize second reader 40, scan and read multi-dose code 6a, and send information to instrument control 24.

Step 3—Compare first read information (e.g., medication code 6a) to second read information (code 6a) and verify information identity. Reject multi-dose container if there is not a match.

Step 4—Locate medication container, customize information 20 as required, initialize writer 16, write information 22A, and repeat from steps for additional containers B-E and information 22B-E as needed/desired. When all containers are encoded, END the process.

Figure 9:
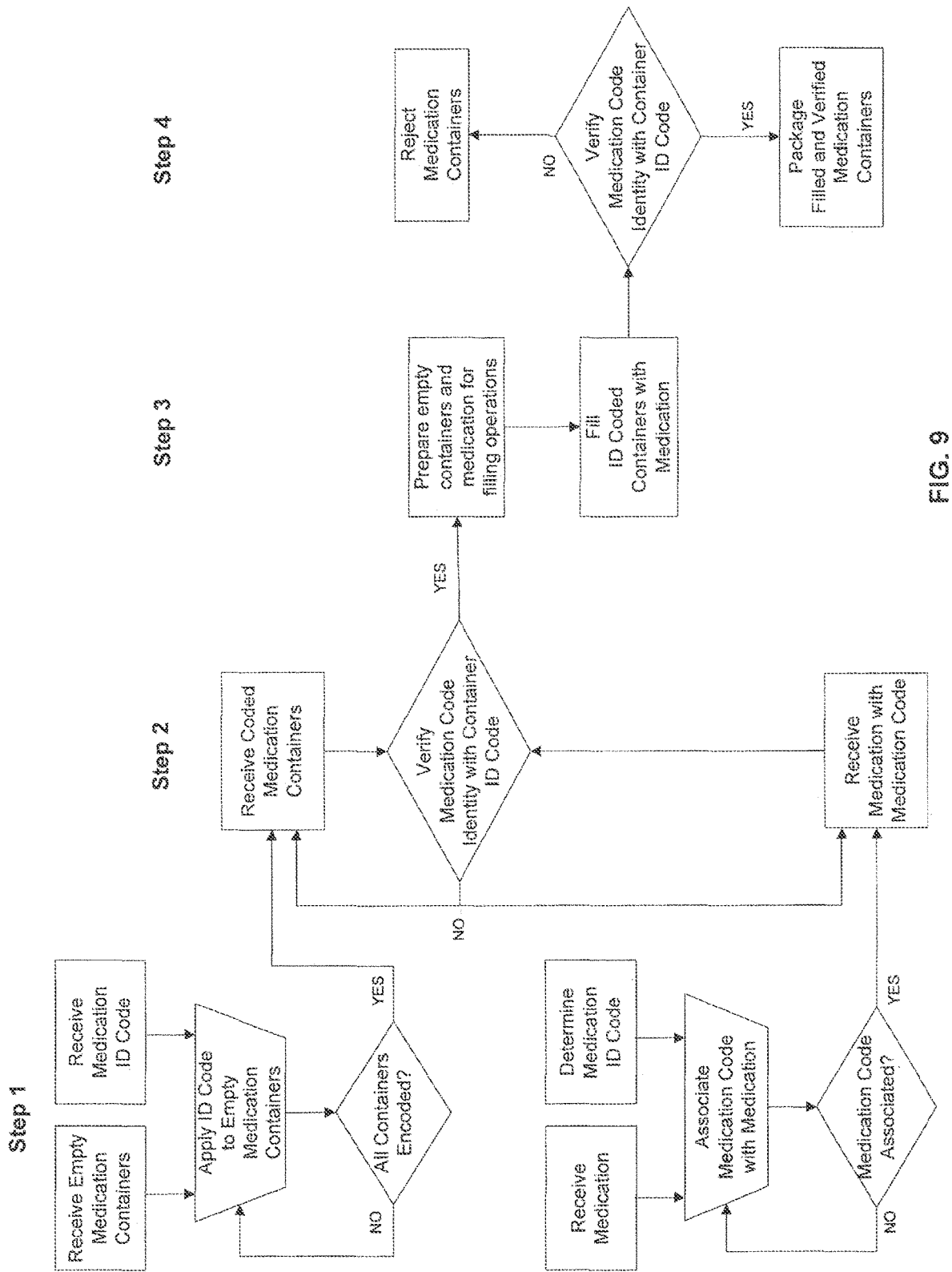
FIG. 9 is an alternate flow diagram illustrating a sequence of steps describing a method and use of an apparatus such as the one in FIG. 1.

FIG. 9 is an alternate process flow diagram to that shown in FIG. 6 relating to the use of a medication identification encoding and verification system 2 such as is shown in FIG. 1. The process can be organized in any number of sequential or parallel steps to accomplish the read ID Code and write ID Code method. One such process is described showing the application of the ID Code to an empty container before a medication is filled into the container. Other process variations can be envisioned that fill the medication into the container before the ID Code is written onto the container (not shown).

Step 1—Prepare empty containers by application of encoded information element and prepare medication for container filling. Empty medication containers are received and inspected for use. Identification ID Code element is received and prepared for application. The ID Code element is written (applied) to the empty container (syringe, vial, bag, etc.). Medication is received and the medication ID Code determined. The ID Code is associated with the medication.

Step 2—Empty encoded containers and coded medication are delivered to an assembly operation. Prior to filling the empty containers with medication, the identity of the medication ID Code can be verified to determine if the ID Code on the empty container is the same as that associated with the medication. If they are the same, proceed to the filling operation. Each and every medication container can be verified or a lot sample can be verified.

Step 3—Empty encoded containers and coded medication are prepared for the filling process. Medication is filled into the empty containers.

Step 4—After filling the empty containers with medication, the identity of the medication ID Code can be verified to determine if the ID Code on the filled container is the same as that associated with the medication. If the identity is the same, proceed to the packaging operation. If there is not identity, the filled containers are rejected.

Figure 10:
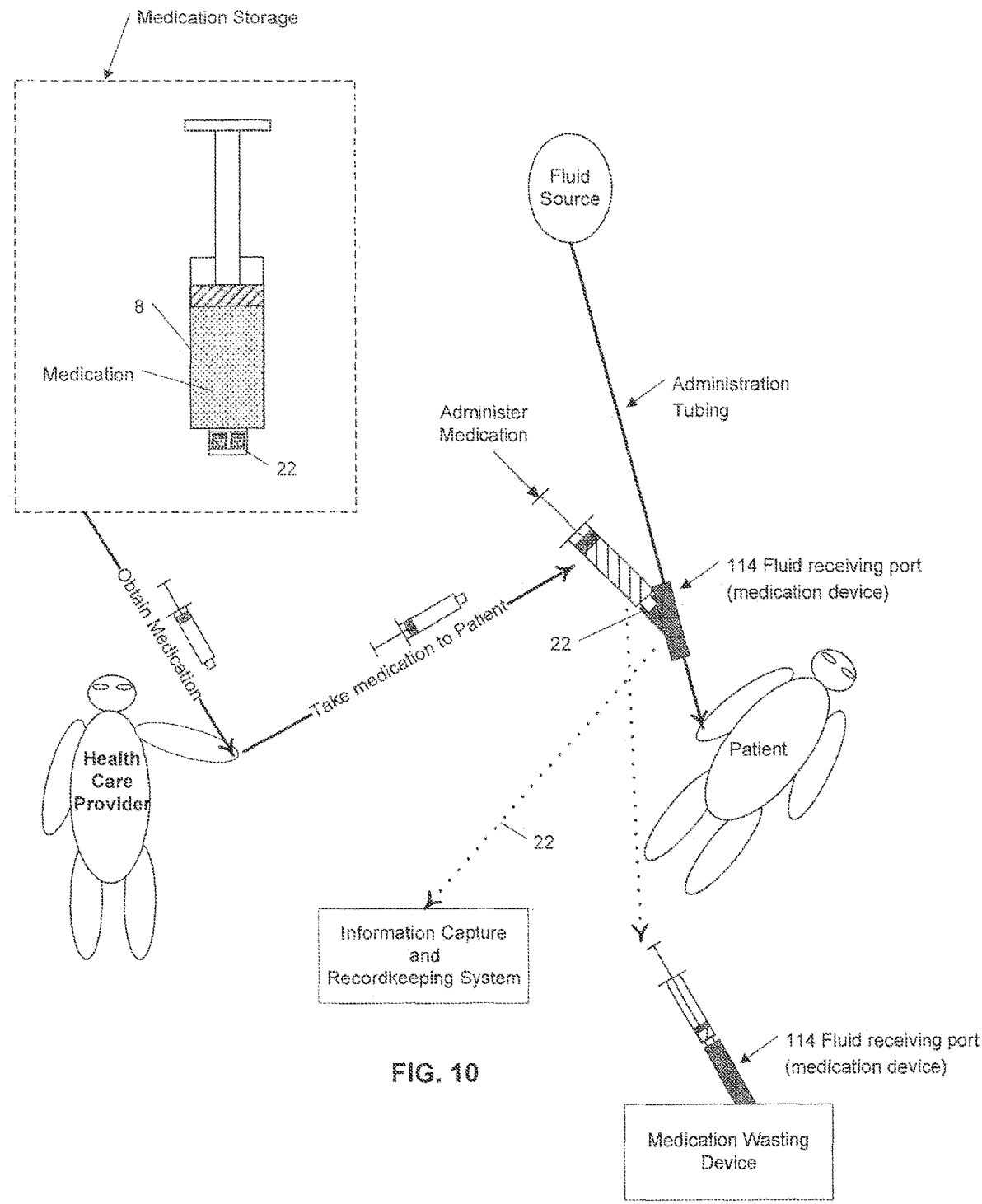
FIG. 10 is a diagram illustrating a sequence of steps a caregiver would use in the administration of medication to a patient.

FIG. 10 illustrates caregiver workflow for administration of medication from the encoded medication container 8. A patient is receiving fluid delivery through an administration tubing set. A fluid receiving port (medication device 114) for medications is attached to the administration tubing close to the patient. During execution of medication delivery, a health care provider obtains a medication container 8 from storage (medication dispensing unit, medication cart, medication kit, etc.). The health care provider takes the medication to the patient and inserts the medication container into the fluid receiving port (medication device 114). Upon attachment the fluid receiving port 114 identifies the medication ID code 20 and transmits the information to an Information Capture and Recordkeeping System. The health care provider then administers the medication to the patient and the medication information encoded within the label is transmitted to the Information Capture and Recordkeeping System, time stamped and recorded. In addition, in some implementations, remaining medication is wasted/disposed in a Medication Wasting Device which can read the medication ID code identifier 22 when the medication container 8 is coupled thereto.

Figure 11:
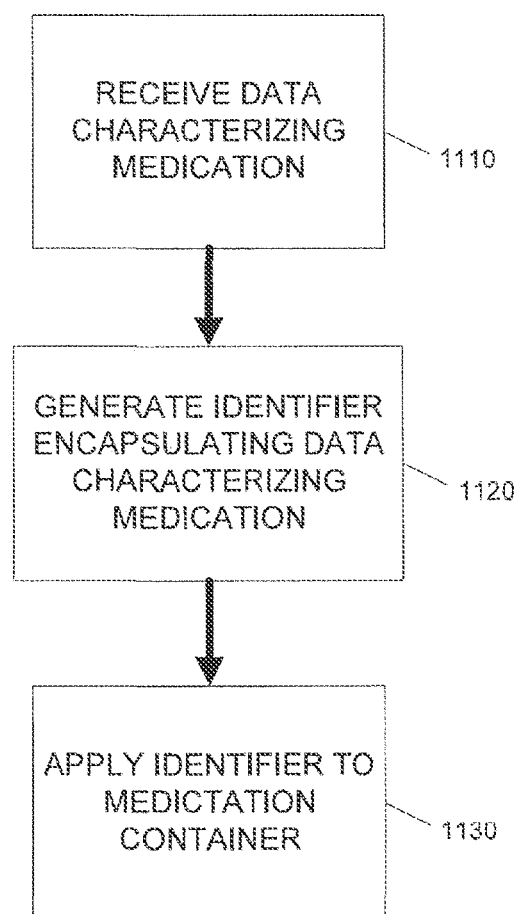
FIG. 11 is a process flow diagram illustrating generation and application of an identifier to a medication container.

FIG. 11 is a process flow diagram illustrating a method 1100 in which, at 1110, data characterizing medication within a medication container is received. Thereafter, at 1120, an identifier encapsulating data characterizing the medication is generated. This identifier is applied, at 1130, to medication container and is positioned such that it is automatically readable by a medication administration device when administering the medication to a patient and/or automatically readable by a medication wasting device when the medication is disposed therein (i.e., the identifier is read without deliberate effort on behalf of a clinician administering the medication to facilitate information transfer between the medication container and the medication administration device).

Figure 12:
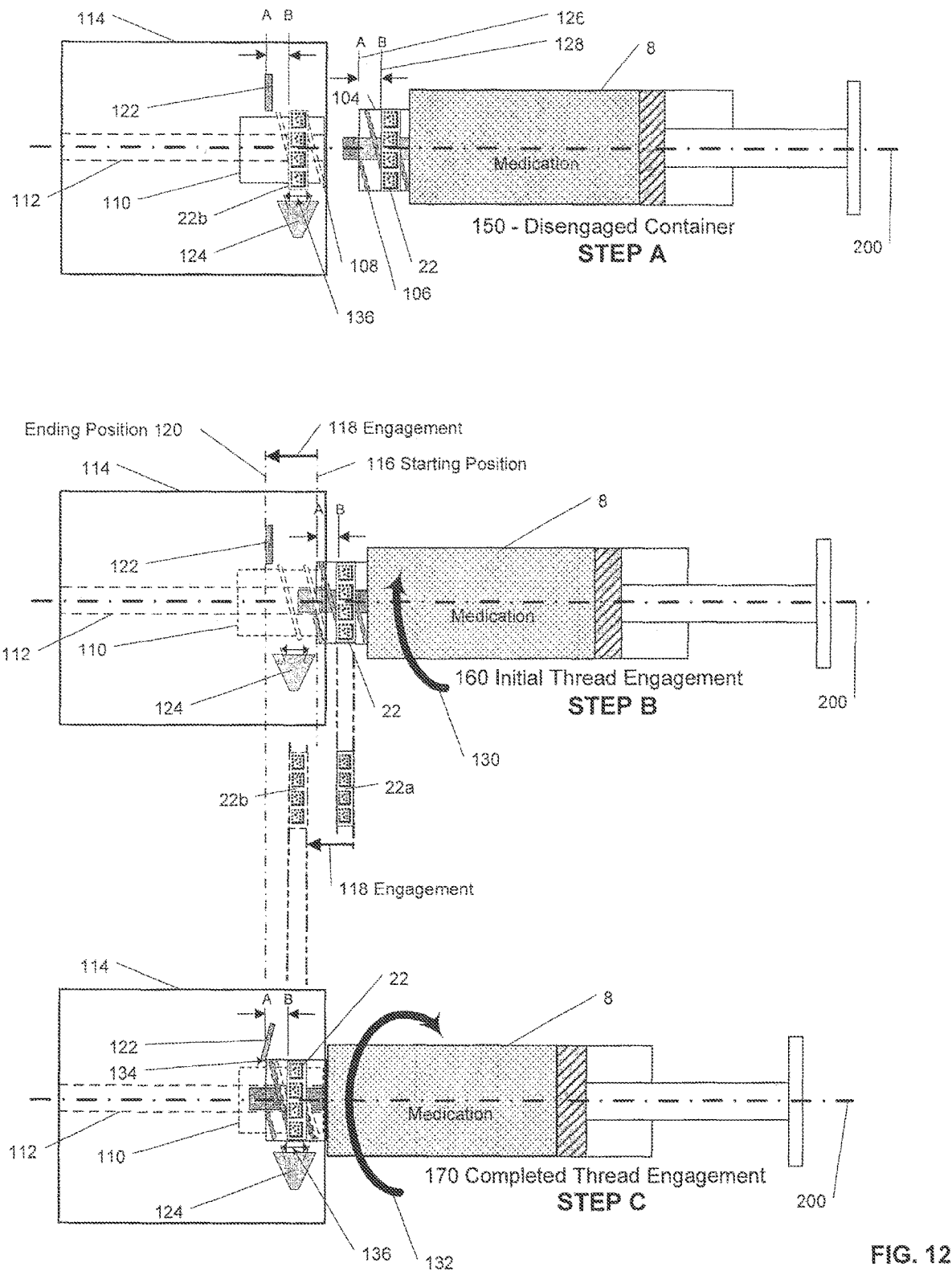
FIG. 12 is an illustration indicating three steps in the attachment of a medication container to a medication administration device.

FIG. 12 is an illustration indicating three steps in the attachment of medication container 8 to a medication device 114. Medication container 8 can have Luer lock surface 104 that provides for application of identifier 22. It is important for the identifier 22 to be positioned accurately (separated by distance A-B) from the leading edge of the Luer lock. This leading edge can be used to trigger activation switch 122 in medication device 114 thus activating sensor 124. The accurate positioning of identifier 22 can be utilized to enable positioning of identifier 22b within the field of view 136 of sensor 124.

In STEP A (150—Disengaged Container) at the top, identifier 22 is positioned relative to the leading edge A 126 of surface 104 at a distance B 128. When fully engaged (see STEP C) identifier 22 is within the field of view/detection 136. To the left of medication container 8 (target for placement of identifier 22) is medication device 114. Within the housing or partially extending from the housing is a female Luer lock port 110 with external locking threads 108. When medication container 8 is engaged with clockwise rotational motion, external threads 108 on medication device 114 can be engaged with internal threads 106 of the male Luer lock fitting 104 of medication container 8. The engagement of the threads can be utilized to move identifier 22 positioned on surface 104 from starting position 116 and ending position 120.

STEP B illustrates initial thread engagement 160 and the start of rotation 130 about axis 200. This rotation and thread engagement translates identifier 22 from position 22a to position 22b moving from a starting position 116 to an ending position 120. When the leading edge of Luer lock 104 reaches the ending position 120, activation of switch 122 happens.

STEP C illustrates a thread engagement 170 after rotation 132 about axis 200 is completed. Rotation 132 is typically greater than 180 degrees of rotation. At this STEP, leading edge 134 of Luer lock surface 104 activates switch 122. Activation of switch 122 initiates sensor 124 detection of identifier 22 now in proper field of view position 136. After full engagement of the Luer lock threads and rotation 132 is complete, flow path 112 is fluidically mated with medication container 8.

Figure 13A:
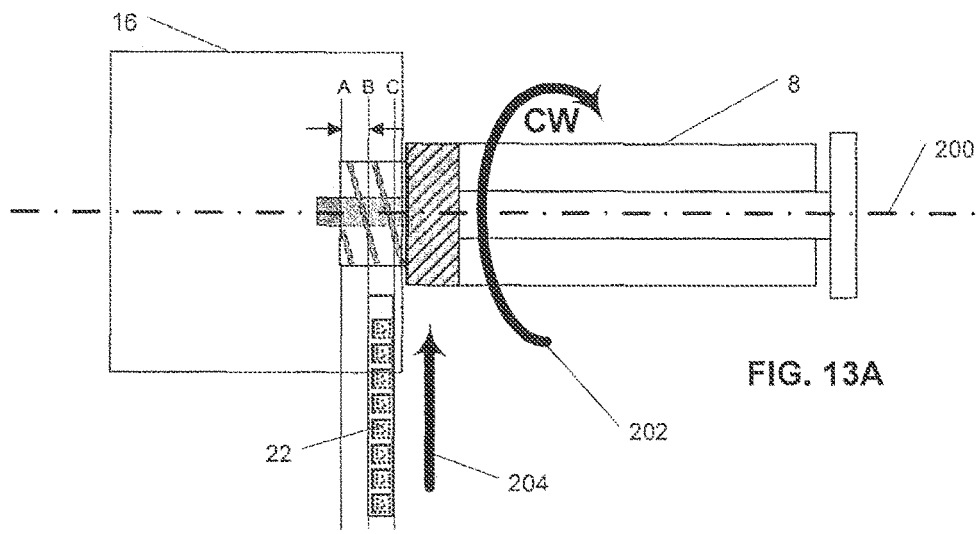
FIGS. 13A-13C are illustrations of applying an identifier to a medication container with rotational motion.
Figure 13B:
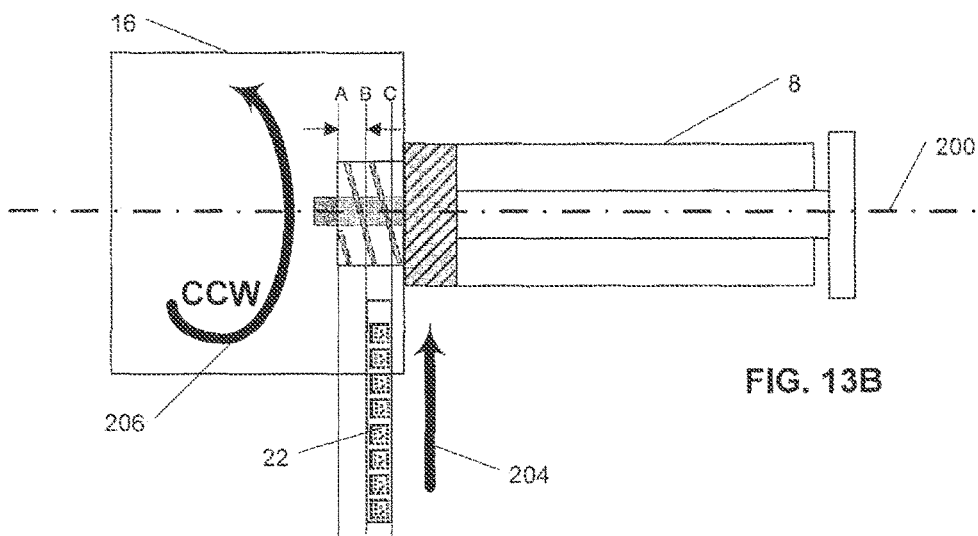
Figure 13C:
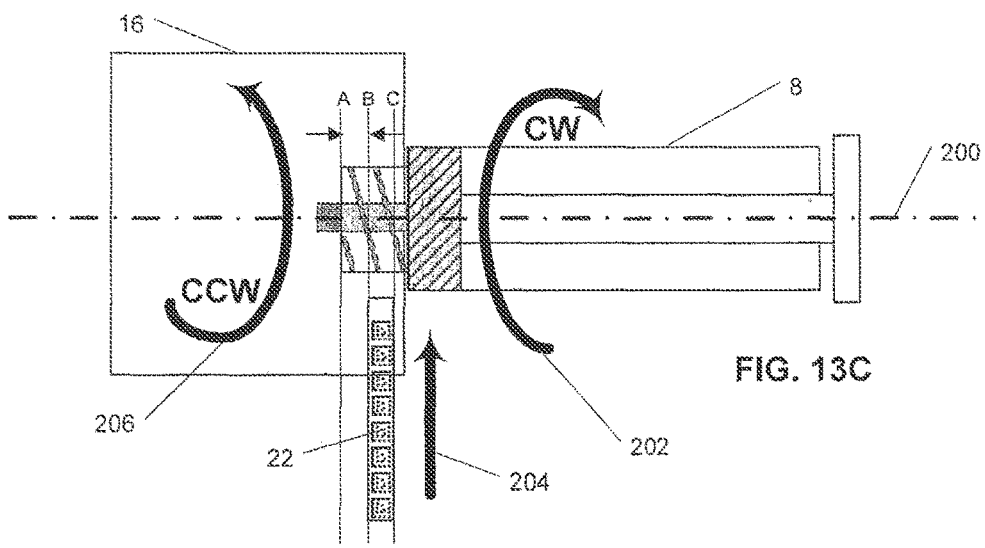

FIGS. 13A-13C are diagrams that illustrate applying an identifier 22 to a medication container 8 with rotational motion. In each figure, identifier 22 is a label and is drawn onto the Luer lock surface 104 by rotational motion. FIG. 13A illustrates a clockwise rotation 202 of medication container 8 and feed direction 204 of label 22. The applicator 16 can remain static and only feeds-in label 22. Alternatively, in FIG. 13B, rotational motion 206 is provided by applicator 16 feeding label 22. Medication container 8 remains static. In yet another alternative shown in FIG. 13C, both medication container 8 and applicator 16 are rotated in opposite directions and label 22 feeds onto surface 104.

Figure 14:
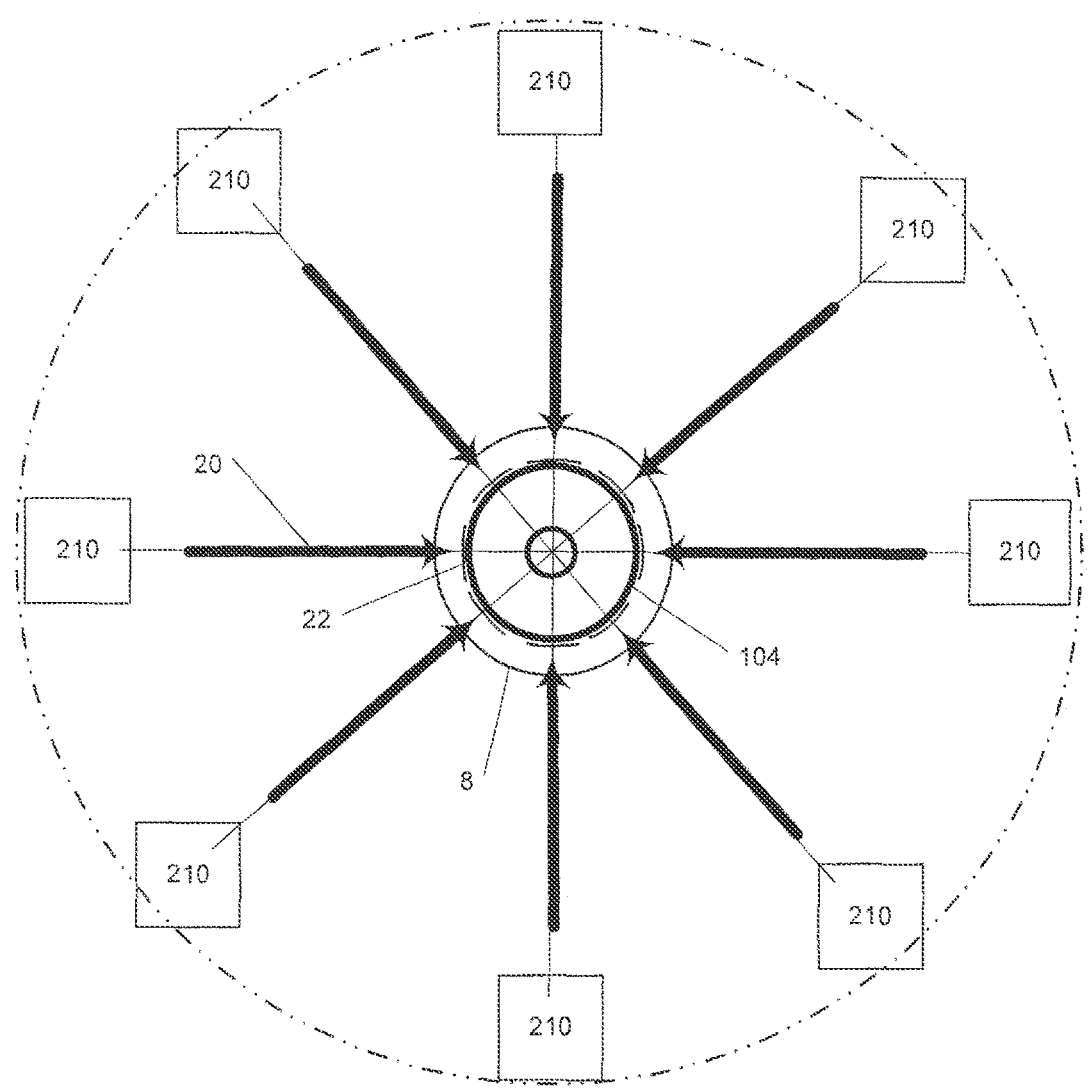
FIG. 14 is an illustration of applying an identifier to a medication container without rotational motion.

In yet another variation shown in FIG. 14, neither medication container 8 nor applicator 16 are rotated. They both remain static with respect to each other. Here, there can be an array of applicators 210 writing information 20 onto Luer lock surface 104. There are eight writing positions shown FIG. 14, each encoding identifier 22 onto the circular surface of medication container 8. This writing process can include laser printing, ink-jet printing, pad printing, thermal transfer printing, laser etching, label placement as well as many others. While shown here with eight applicators 210, more or less identifiers 22 images can be applied by more or less applicators 210.

Figure 15:
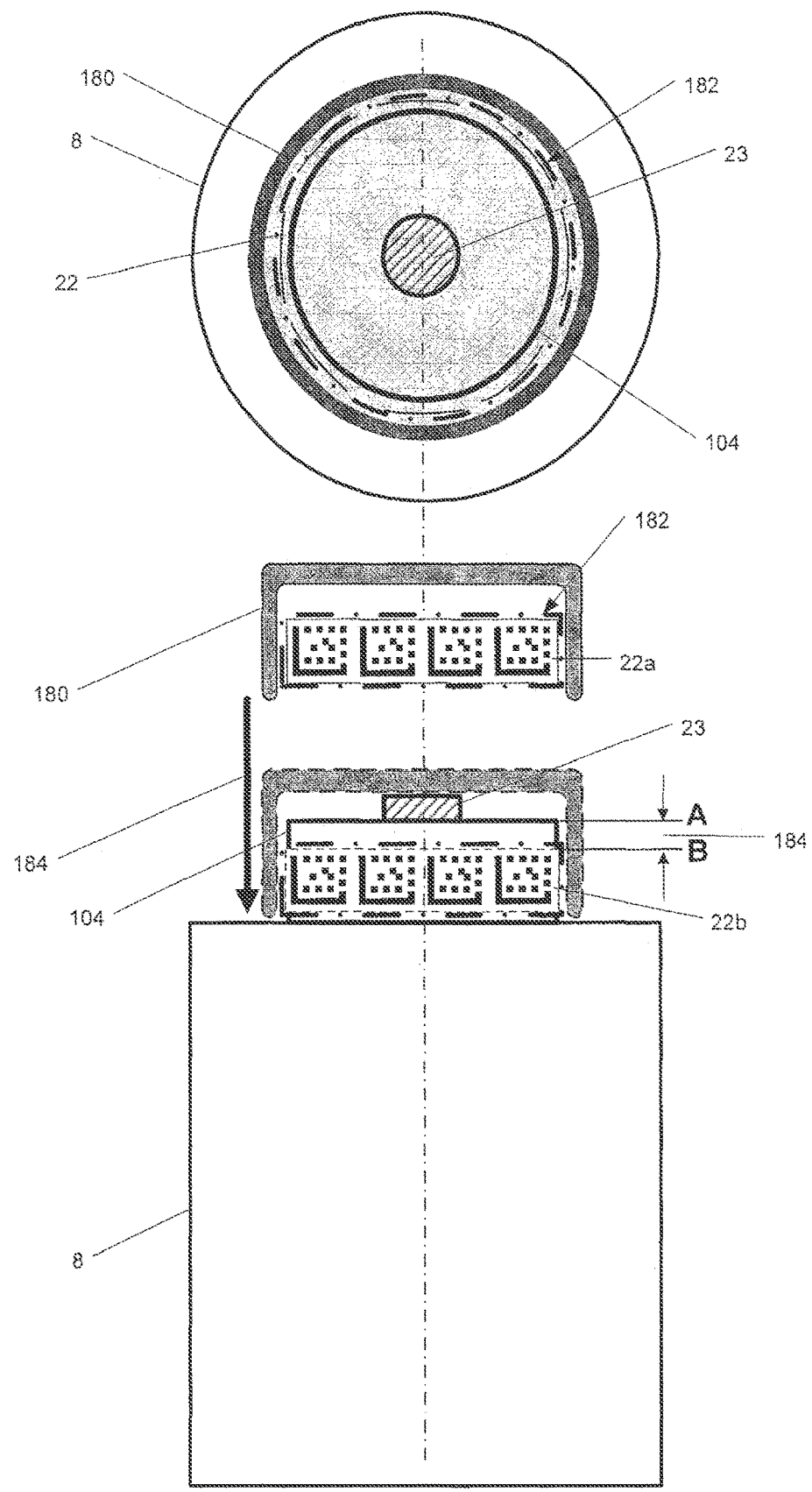
FIG. 15 is an illustration of applying an identifier to a medication container with a cap.

FIG. 15 is an illustration of applying an identifier 22 to a medication container 8 with a cap 180. Shown at the top is a concentric illustration of the location of identifier 22 contained within cap 180. An identifier carrier 182 can be placed inside cap 180 such that when cap 180 is placed over fluid outlet 23 (action 184) the identifier carrier 182 is securely fixed onto surface 104. Cap 180 positions identifier 22 in precise position 184 maintaining distance A-B.

Figure 16A:
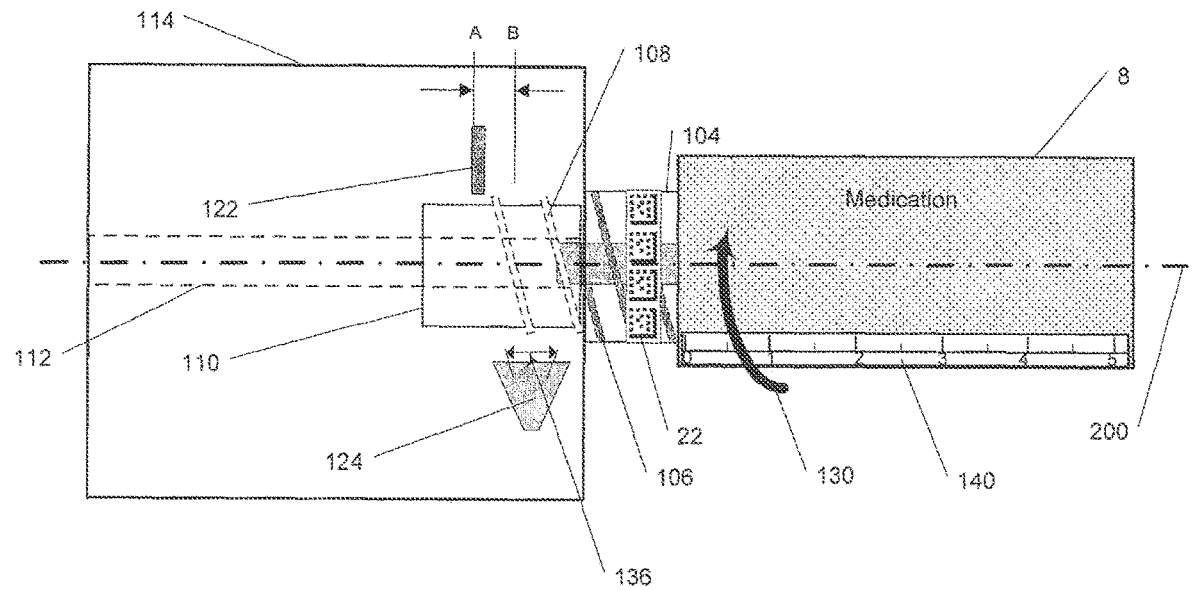
FIGS. 16A and 16B are illustrations indicating alignment of graduations with Luer lock threads.
Figure 16B:
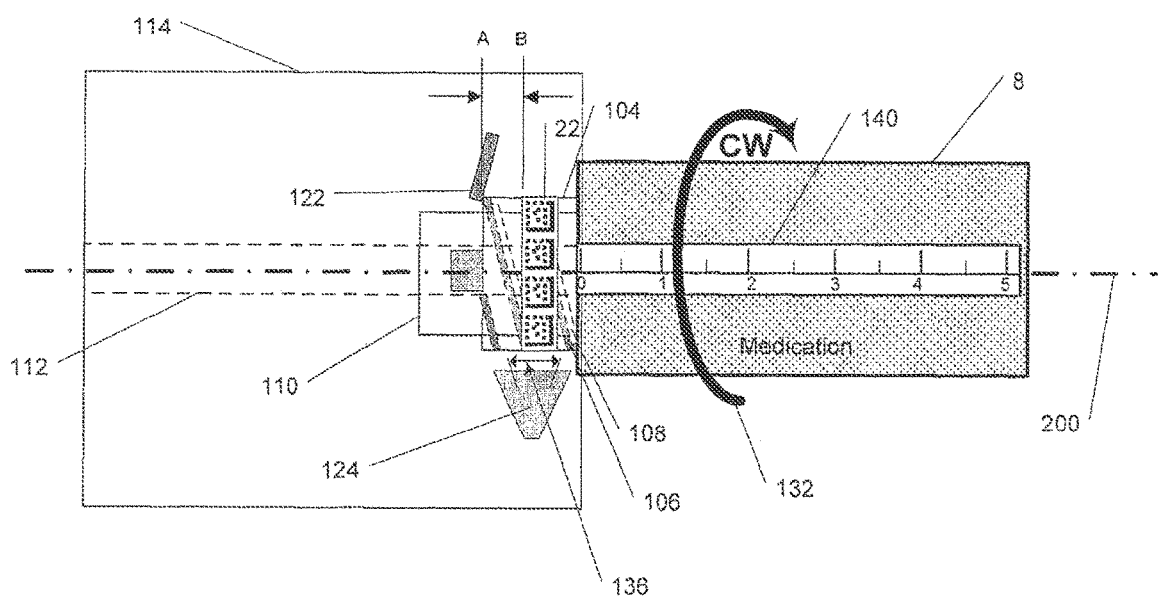

FIGS. 16A and 16B are illustrations indicating alignment of medication container 8 graduations 140 with the male Luer lock internal threads 106. Users frequently observe graduations on medication containers to identify how much medication has been administered to the patient. FIG. 16A shows medication container 8 about to attach to medication device 114 (medication port). Graduations 140 are barely visible. Engagement can be initiated with rotational motion 130 about axis 200 and male Luer lock threads 106 on medication container 8 will begin to engage the female Luer lock threads 108 on medication device 114 (fluid port).

Moving to FIG. 16B, if the graduation marks 140 on medication container 8 are aligned properly with threads 106, then when full engagement is complete following rotation 132 the graduations 140 will end up in an easy viewing position for the user. This is particularly important when medication device 114 is held in a fixed position (fixed manifold or port in anesthesia or an intensive care environment). Proper alignment of the male Luer lock threads 106 on medication container 8 and known female Luer lock thread position 108 on medication device 114 can assure graduations are in viewing position.

Figure 17:
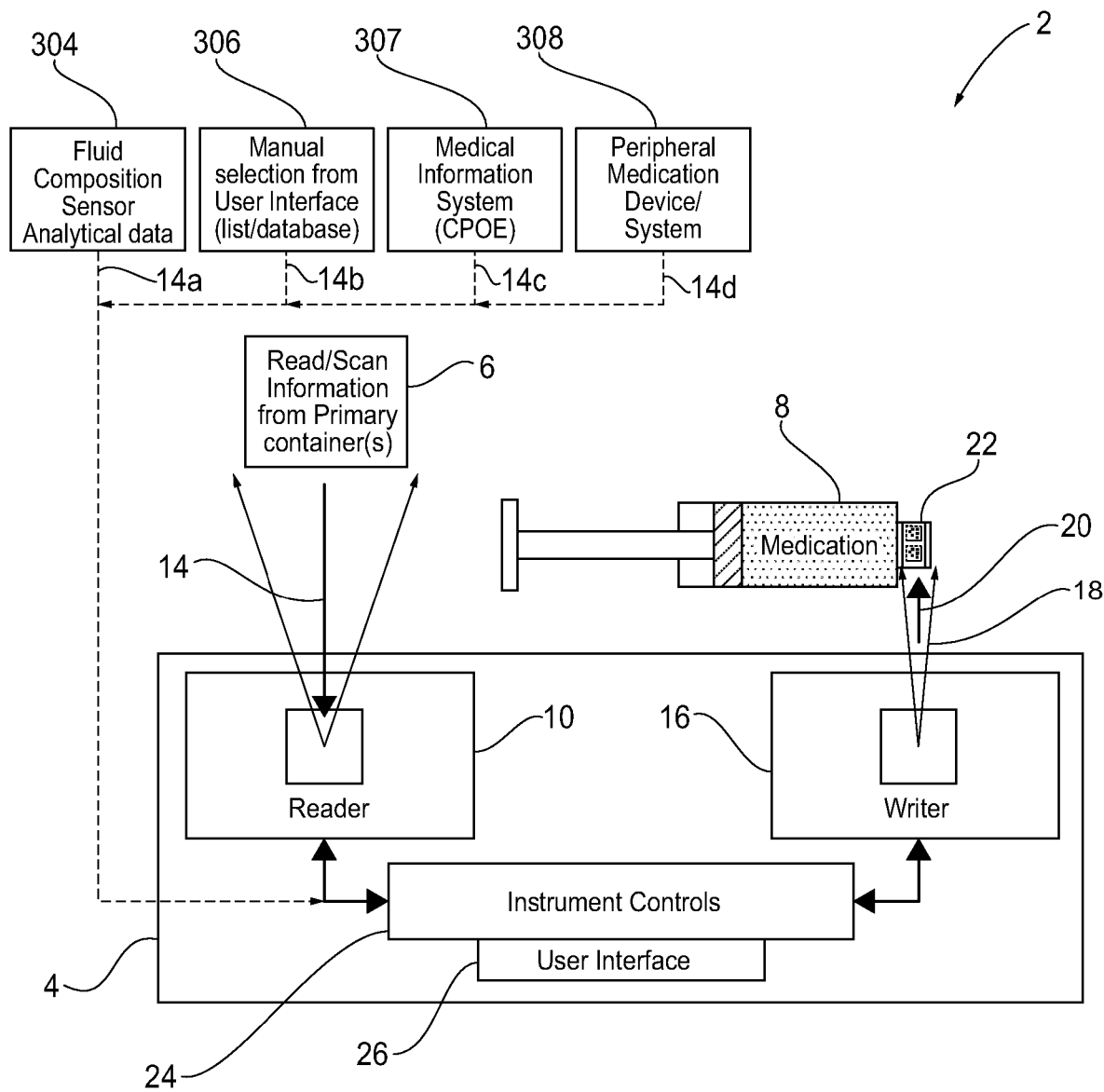
FIG. 17 illustrates the use of multiple data sources to provide identifier information input.

FIG. 17 is a diagram illustrating the use of additional medication information sources to be used independently or complementary to medication source code 6 in creating identifier 22. In some embodiments, medication identification information 14, generated by reading medication source code 6, can directly or indirectly be used as the primary input data source for determining the medication identification information 20 used to encode identifier 22. In further variations, a number of other potential input data sources can also be used to provide input to the medication identification information 20 data set used to encode identifier 22.

For example, a fluid composition sensor 304 can be used to analytically determine one or more fluid constituents and their relative concentrations contained in a primarily medication container. Fluid composition sensing technologies can include but are not limited to spectroscopy, photometric analysis, electrometric analysis (e.g. impedance, admittance, conductivity), chromatography, high performance liquid chromatography, mass spectroscopy, physical property measurements, or parametric analysis based on a combination of the previously listed technologies. Fluid composition sensor 304 can produce output data medication composition information 14a which can be used for identification and/or verification of proper filling and labeling of information target 8. As used herein, unless otherwise stated, the term "medication" can represent a therapeutic fluid containing multiple constituents in various relative concentrations.

Stated differently, in one variation, the fluid composition sensor 304 can determine the composition of fluid within the medication container 8 (via measurements) prior to any identifier being applied thereto. Based on such a determination, either a custom identifier can be generated (e.g., an identifier encapsulating the measured composition, etc.) or the composition can be associated with a pre-existing identifier associated with the particular composition within the medication container. In addition or in the alternative, the composition of fluid within the medication container 8 can be determined by the fluid composition sensor 304 prior to the identifier 22 being applied to the medication container 8. This measurement can be used to verify that the composition matches the data encapsulated or referenced by the identifier 22.

Another source of input data, can be a manually selected data set 306 chosen by a user involved in a medication filling and/or labeling operation. Formularies, drug libraries, industry standard drug vocabularies (e.g. First Databank) and other lists of medication information are commonly stored in electronic databases. Database records for medications stored in such lists can include the same or similar data elements as those listed for medication source code 6. A user involved in a medication filling and/or labeling operation can access database records using a computer or other user interface device and manually identify appropriate medication information, referred herein as manual selection information 14b they want used as input creating identifier 22. Manual selection information 14b can be a single data element or a data set, it can be used as a compliment to or substitute for medication identification information 14, and/or can correspond to characteristics of a primary, interim, or secondary medication container.

A third source of input data, can be a medical information system 307. Particularly in instances where the secondary medication container bearing identifier 22 contains patient-specific medication contents, a medical information system 307 can provide system medication information 14c data which can include a medication filling request, patient-specific information, medication information, and/or administration instructions. For example, if the filling and labeling of a secondary medication container bearing identifier 22 is to be performed within a hospital pharmacy, a physician can use a Computerized Physician Order Entry (CPOE) system to prescribe the medication and initiate the process of appropriately filling a medication container to execute the prescribed order. The process could also be initiated by a pharmacist approving a medication order queued in a Pharmacy Information System (PIS). In both cases, system medication information 14c can include details contained in a typical patient medication order, including but not limited to, patient identification information, medication information, and medication administration instructions. A pharmacist in a hospital pharmacy that receives an order requiring the filling and labeling of a secondary container and can, if appropriate, chose to identify and additionally add manual selection information 14b to compliment system medication information 14c as contributing data used in creating identifier 22 for the secondary container. This illustrative example further exemplifies the multitude of ways various information sources can be used in combination when creating an identifier 22.

Figure 19:
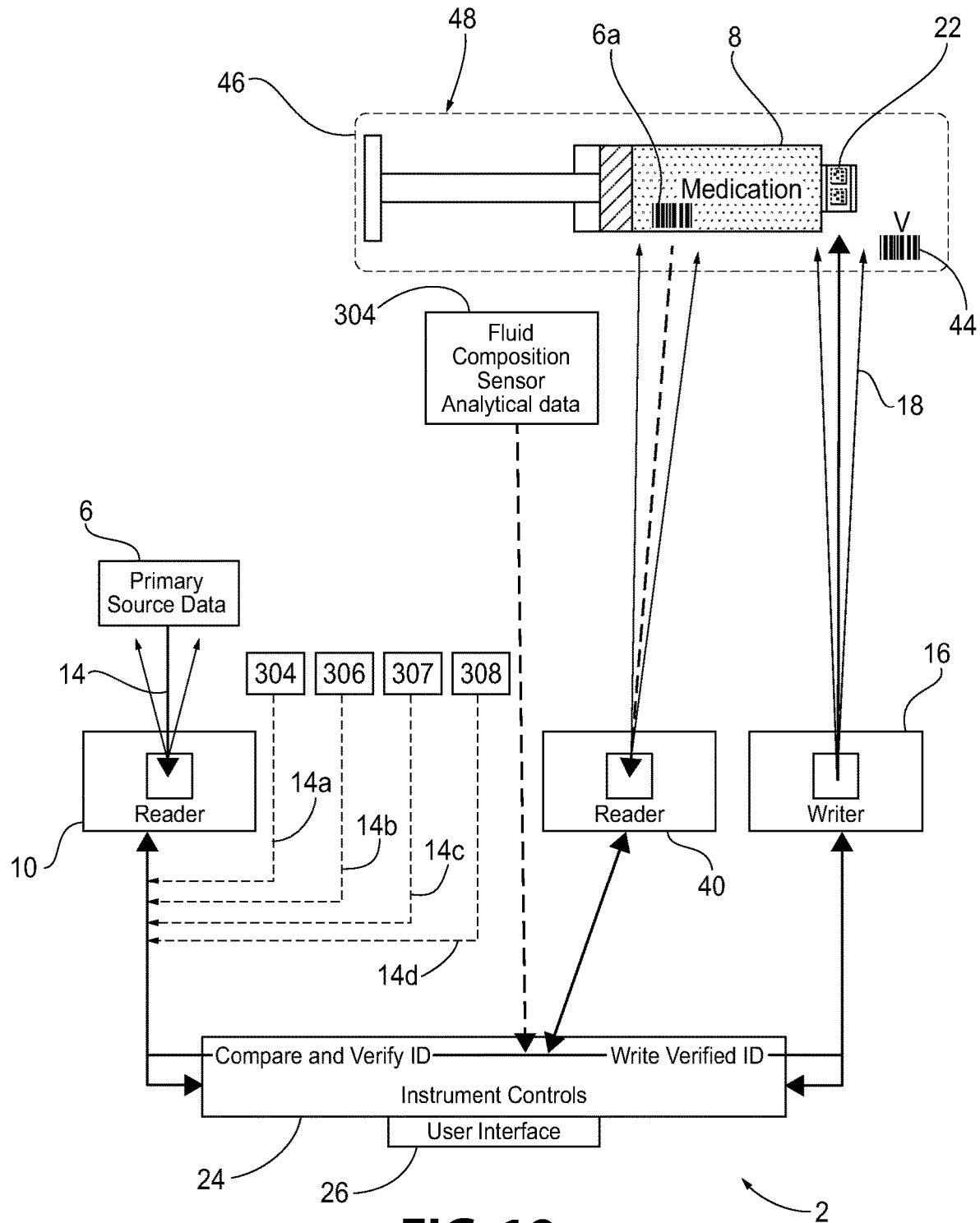
FIG. 19 illustrates the use of distributed methods, technologies and components to implement an overall medication container encoding, verification and identification process.

Yet another source of input data, which will be further described in FIG. 19, can be medication filling information 14d generated by peripheral medication device/system 308 involved in the overall medication filling and labeling process. For example, a pharmaceutical manufacturer of pre-filled syringes can have an existing piece of equipment that upon filling a syringe to be transferred to an apparatus for applying identifier 22, automatically sends medication filling information 14b to instrumentation controls 24 to subsequently be used in creating identifier 22 for the filled syringe.

Figure 18:
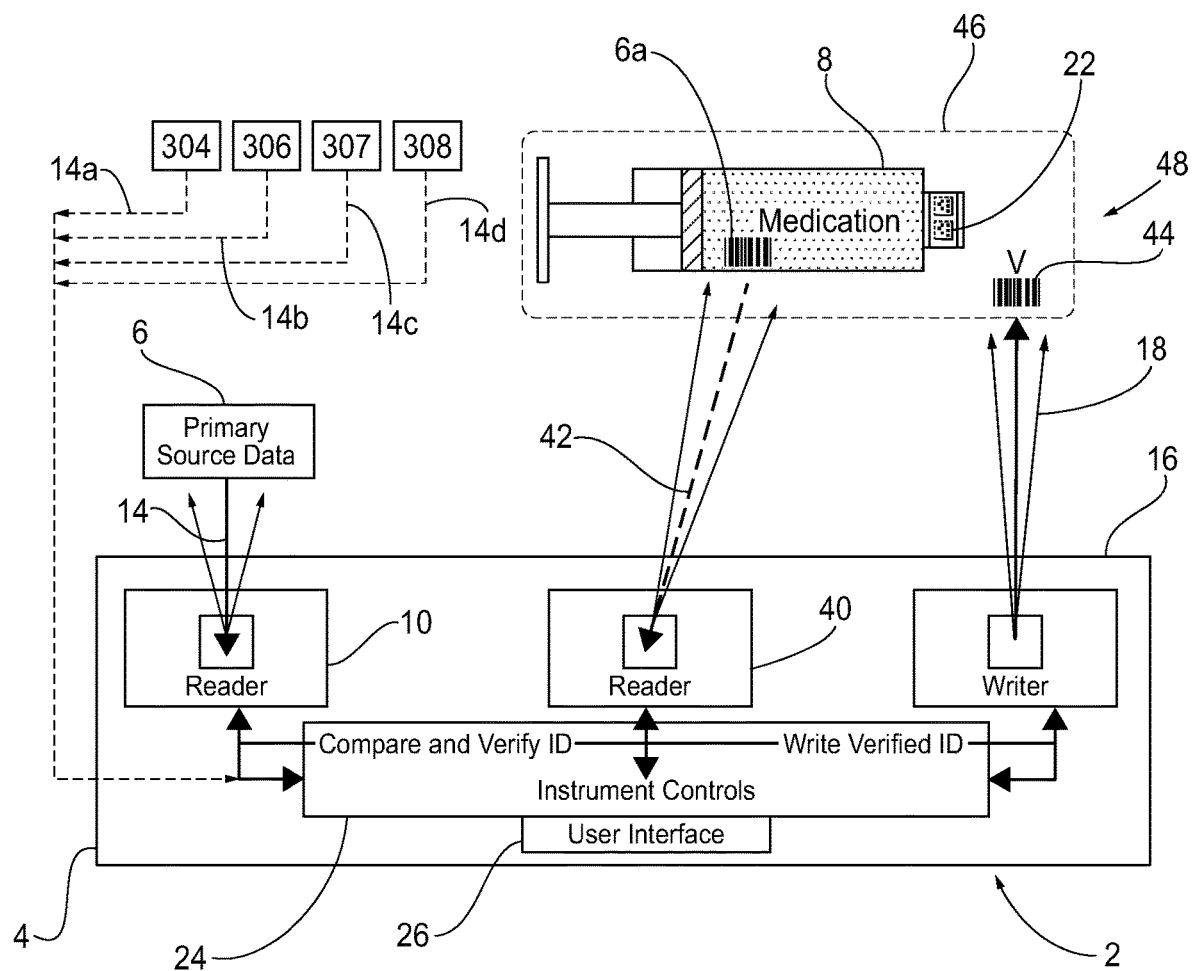
FIG. 18 illustrates the use of alternate information sources and methods for verification of proper information and/or medication transfer.

FIG. 18 illustrates the use of alternate information sources and methods for verifying the integrity of information and medication transfer at various stages of a process used to fill a medication container bearing identifier 22. FIG. 18 applies similar concepts and methods such as those illustrated in FIG. 17 to expand the range of potential input data used in the process thus expanding the range of alternative verification embodiments. For example, if fluid composition sensor 304 is used to determine the type and relative concentrations of fluid constituents in a primary medication container, then the same instrument, or a separate fluid composition sensor 304, can be used to verify that the type and relative concentrations of fluid constituents in a secondary container bearing identifier 22 match those of the primary medication container following a medication transfer from the primary container to the secondary container. This verification can be accomplished by instrument controls 24 comparing the primary fluid composition information 14a matches the secondary fluid composition information 14a. Similarly, manual selection information 14b, system medication information 14c, and peripheral medication device/system information 14d can be used independently or in combination to verify that information encoded in identifier 22 on information target 8 is correct.

FIG. 19 illustrates the use of distributed methods, technologies and components to implement an overall medication container encoding, verification and identification process. In one variation utilizing a 3-stage process utilizing distributed components, a device, system or apparatus produced by a first manufacturer can be used for reading primary source data 6 from a primary medication container and transferring medication from the primary medication container into a secondary medication container that will serve as information target 8 for identifier 22 during a later stage in the process (stage 1); then a composition sensor instrument from a second manufacturer can be used to sample and verify a match between the fluid contents in the primary and secondary containers (stage 2); followed by the use of another device, system or apparatus from a third manufacturer to apply identifier 22 to the prefilled information target 8 and verify there is proper correlation between the information encoded in identifier 22 and primary source data 6 (stage 3). A further variation of distributed components that is represented in the previous example, can involve the subdividing of functional blocks such as having the overall role and control logic of instrument controls 24 distributed among the controls systems of the three independent instruments used in the three process stages.

In another variant which illustrates the use of distributed technologies, information from sources such as fluid composition sensor 304, manually selected data set 306, or medical information system 307; and information receivers such as instrument controls 24, and writer 16; can be transferred between stages of the overall medication container encoding, verification and identification process by various interchangeable technology approaches. For example, the output of fluid composition sensor 304 can be transferred into instrument controls 24 by (1) producing a barcode that is later read by reader 10, (2) electronically sending the information over a network or electrical interface connection, or (3) output into a printed report that a user can use to manually enter appropriate information elements into user interface 26.

The concept of distributed methods relates to all elements and or steps involved in the overall medication container encoding, verification and identification process, including but not limited to: physical separation of tangible elements; subdivision or combination of functional blocks and/or functional logic; and, the use and/or mix of various technologies for transferring information or data from one area to another. Technologies for transferring information also include human observable formats such as photos, videos, forms and labels.

Figure 20:
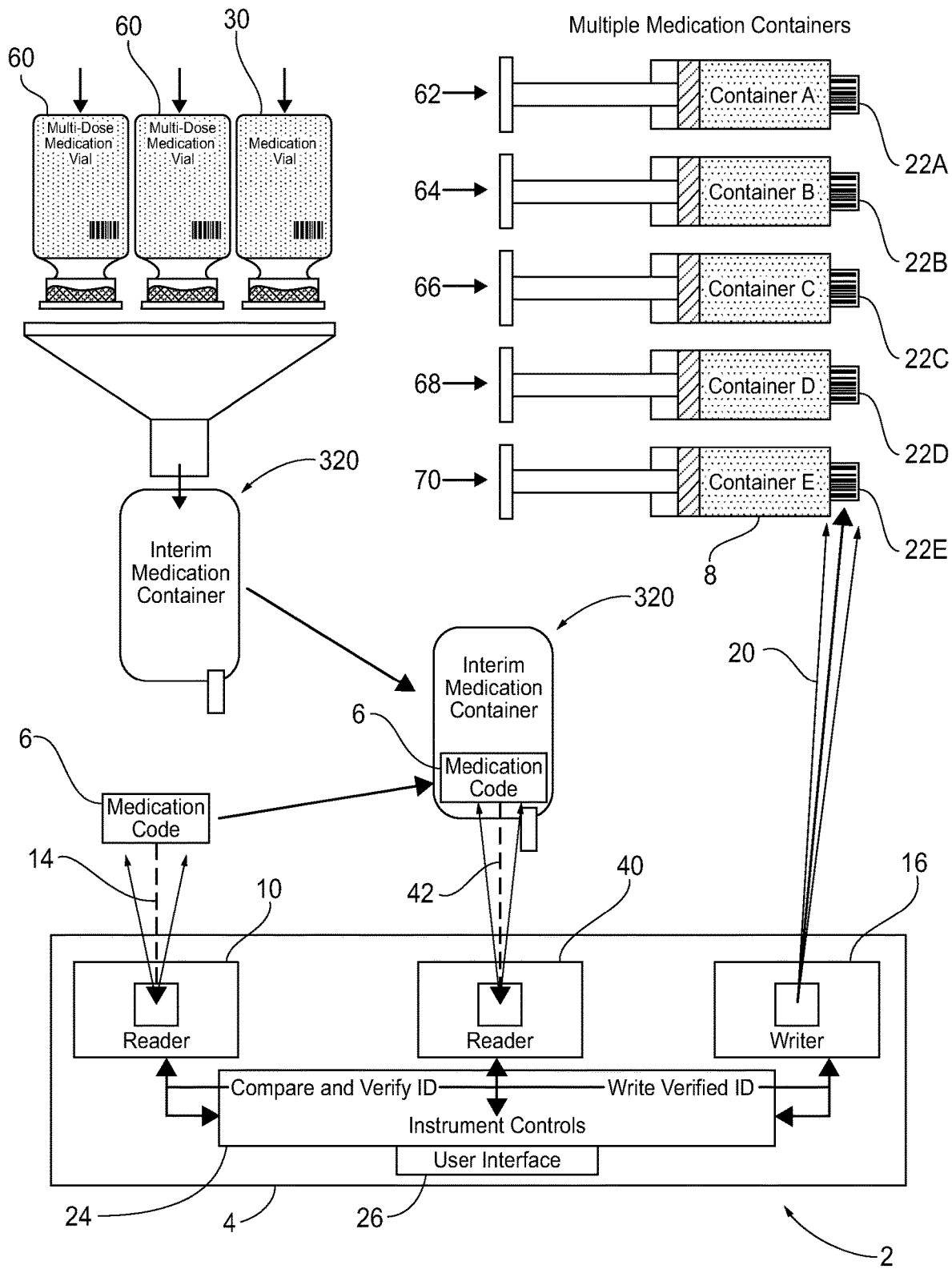
FIG. 20 illustrates a process involving use of an interim bulk medication container used to fill secondary medication containers.

FIG. 20 illustrates a method involving use of an interim bulk medication container used to fill secondary medication containers. The methodology illustrated in FIG. 20 builds upon of the methodology described in FIG. 7 which uses a larger, primary multi-dose medication container 60 to fill multiple secondary medication containers 62, 64, 66, 68, and 70, each bearing encoded identifier information 22A, 22B, 22C, 22D, and 22E, respectively. In FIG. 20, the fluid contents of one or more standard vials 30 and/or multi-dose medication containers 60, can be combined into one or more interim medication containers 320 which can be used to the fill secondary medication containers. Vials 30 and/or multi-dose medication containers 60 can each contain the same medication or they can contain multiple medications and/or other fluid constituents used to fill the secondary containers. Interim medication container 320 can be filled with multiple medication containers of a single medication and a diluents to accomplish the filling of secondary containers that can contain diluted forms of the primary source medication. Interim medication container 320 can also be filled with a mixture involving multiple medications containers to compound a multi-constituent medication. Examples of such compounded medications include compounding of Glycopyrrolate-Neostigmine injections and patient-specific total parenteral nutrition (TPN) solutions.

When an interim medication container 320 is used, that container acts as a secondary medication container relative to the primary medication containers vials 30 and multi-dose vials 60. As such, the principles and methods previously described for the encoding, labeling and verification of secondary containers can be applied filling, checking and labeling of interim medication container 320. Simultaneously, interim medication container 320 acts as a primary medication container relative to the target secondary medication containers 62, 64, 66, 68, and 70, each bearing encoded identifier information 22A, 22B, 22C, 22D, and 22E, respectively.

Features and functions of a sample medication container encoded fluid outlet and the use of same by a medication injection site/medication administration device are detailed in the U.S. patent application Ser. Nos. 12/614,276, 12/765,707, and 12/938,300 all entitled "MEDICATION INJECTION SITE AND DATA COLLECTION SYSTEM". Features and functions of a sample vial adapter and encoded fluid transfer element are detailed in U.S. patent application Ser. Nos. 12/768,509 and 13/282,255, both entitled "MEDICATION AND IDENTIFICATION INFORMATION TRANSFER APPARATUS". Other applications useful for implementing the subject matter described herein include: U.S. patent application Ser. No. 13/524,736 entitled: "Medication Dose Preparation and Transfer System", and U.S. patent application Ser. No. 13/549,278 entitled: "Characterizing Medication Container Preparation, Use, And Disposal Within A Clinical Workflow". The contents of each of the aforementioned applications are hereby fully incorporated by reference. Other medication containers and/or vial adapters and fluid transfer elements may be implemented with this read-write encoding system.

In addition, while the foregoing examples are mainly directed to the preparation and administration of medication within medication containers, it will be appreciated that the same concepts can be applied to a medication wasting device. For example, a medication wasting device can be configured to receive a syringe containing a controlled substance and bearing an identifier such that the identifier is automatically read by the medication wasting device when the syringe is coupled thereto. One example of a medication wasting device is described in U.S. Pat. App. Ser. No. 61/358,937 and Ser. No. 13/170,073 both entitled: "Medication Waste Collection Apparatus", the contents of both applications are hereby fully incorporated by reference.

Various implementations of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e.g., mouse, touch screen, etc.), and at least one output device.

These computer programs, which can also be referred to programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, the subject matter described herein can be implemented on a computer having a display device, such as for example a cathode ray tube (CRT) or a liquid crystal display (LCD) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

The computing system may include clients and servers. A client and server are generally remote from each other and typically interact through a communication network. The relationship of client and server arises by virtue of computer programs running on the respective computers and having a client-server relationship to each other.

The implementations set forth in the foregoing description do not represent all implementations consistent with the subject matter described herein. Instead, they are merely some examples consistent with aspects related to the described subject matter. Wherever possible, the same reference numbers will be used throughout the drawings to refer to the same or like parts.

Although a few variations have been described in detail above, other modifications or additions are possible. In particular, further features and/or variations can be provided in addition to those set forth herein. For example, the implementations described above can be directed to various combinations and sub-combinations of the disclosed features and/or combinations and sub-combinations of several further features disclosed above. In addition, the logic flows and steps for use described herein do not require the particular order shown, or sequential order, to achieve desirable results. Other embodiments can be within the scope of the following claims.

What is claimed is:

1. A computer-implemented method comprising:
    obtaining, with at least one processor, from a medication information source, medication identification information associated with a first medication container;
    obtaining, with at least one processor, from at least one additional medication information source, additional medication information; and
    generating, with at least one processor, based on the medication identification information and the additional medication information, encoded medication identification information for encoding an identifier associated with a second medication container,
wherein the obtaining the additional medication information further includes:
obtaining, with at least one processor, from a fluid composition sensor, medication composition information associated with one or more fluid constituents and relative concentrations of the one or more fluid constituents contained in the first medication container, wherein the encoded medication identification information is further generated based on the medication composition information, and
wherein the method further comprises:
measuring, with the fluid composition sensor, the one or more fluid constituents and the relative concentrations of the one or more fluid constituents contained in the first medication container.

2. The computer-implemented method of claim 1, wherein the medication identification information includes the one or more fluid constituents and the relative concentrations of the one or more fluid constituents contained in the first medication container, the method further comprising:
verifying, with at least one processor, based on the medication composition information and the medication identification information, that the one or more fluid constituents and the relative concentrations of the one or more fluid constituents included in the medication identification information matches the one or more fluid constituents and the relative concentrations of the one or more fluid constituents included in the medication composition information.

3. The computer-implemented method of claim 1, wherein obtaining, from at least one additional medication information source, the additional medication information further includes:
receiving, with at least one processor, via a user interface, a user selection of a data set of a plurality of data sets stored in an electronic database; and
obtaining, with at least one processor, the user selected data set from the electronic database, wherein the encoded medication identification information is further generated based on the user selected data set.

4. The computer-implemented method of claim 3, wherein the user selected data set includes at least one of the following: a formulary, a drug library, an industry standard drug vocabulary, or any combination thereof.

5. The computer-implemented method of claim 1, wherein obtaining, from at least one additional medication information source, the additional medication information further includes:
obtaining, with at least one processor, system medication information associated with a patient medication order including at least one of the following: a medication filling request, patient-specific information, medication administration instructions, or any combination thereof, wherein the encoded medication identification information is further generated based on the system medication information.

6. The computer-implemented method of claim 1, wherein obtaining, from at least one additional medication information source, the additional medication information further includes:
receiving, with at least one processor, from a peripheral medication device used to fill the first medication container, medication filling information associated with the first medication container, wherein the encoded medication information is further generated based on the medication filling information.

7. The computer-implemented method of claim 6, further comprising:
filling, with the peripheral medication device, the first medication container with a medication;
in response to filling the first medication container with the medication, automatically transmitting, with the peripheral medication device, to at least one processor external to the peripheral medication device, the medication filling information.

8. The computer-implemented method of claim 1, wherein the medication identification information includes the one or more fluid constituents and the relative concentrations of the one or more fluid constituents contained in the first medication container, the method further comprising:
obtaining, with at least one processor, from the fluid composition sensor, further medication composition information associated with one or more fluid constituents and relative concentrations of the one or more fluid constituents contained in the second medication container; and
verifying, with at least one processor, based on the further medication composition information and the medication identification information, that the one or more fluid constituents and the relative concentrations of the one or more fluid constituents included in the medication identification information matches the one or more fluid constituents and the relative concentrations of the one or more fluid constituents included in the further medication composition information.

9. The computer-implemented method of claim 1, further comprising:
writing, with a writer device, the encoded medication identification information to an identifier associated with the second medication container.

10. The computer-implemented method of claim 9, wherein writer device includes an RFID writer, and wherein the identifier includes an RFID tag.

11. The computer-implemented method of claim 1, wherein obtaining, from at least one additional medication information source, the additional medication information further includes:
receiving, via a user interface, a user selection of a data set of a plurality of data sets stored in an electronic database;
obtaining the user selected data set from the electronic database, wherein the encoded medication identification information is further generated based on the user selected data set;
obtaining system medication information associated with a patient medication order including at least one of the following: a medication filling request, patient-specific information, medication administration instructions, or any combination thereof, wherein the encoded medication identification information is further generated based on the system medication information; and
receiving, from a peripheral medication device used to fill the first medication container, medication filling information associated with the first medication container, wherein the encoded medication information is further generated based on the medication filling information.

12. A system comprising:
one or more processors programmed and/or configured to:
obtain, from a medication information source, medication identification information associated with a first medication container;

obtain, from at least one additional medication information source, additional medication information; and generate, based on the medication identification information and the additional medication information, encoded medication identification information for encoding an identifier associated with a second medication container, wherein the one or more processors are further programmed and/or configured obtain, from the at least one additional medication information source, the additional medication information by:

obtaining, from a fluid composition sensor, medication composition information associated with one or more fluid constituents and relative concentrations of the one or more fluid constituents contained in the first medication container, wherein the encoded medication identification information is further generated based on the medication composition information;

receiving, via a user interface, a user selection of a data set of a plurality of data sets stored in an electronic database;

obtaining the user selected data set from the electronic database, wherein the encoded medication identification information is further generated based on the user selected data set;

obtaining system medication information associated with a patient medication order including at least one of the following: a medication filling request, patient-specific information, medication administration instructions, or any combination thereof, wherein the encoded medication identification information is further generated based on the system medication information; and receiving, from a peripheral medication device used to fill the first medication container, medication filling information associated with the first medication container, wherein the encoded medication information is further generated based on the medication filling information, wherein the system further comprises:

the fluid composition sensor configured to measure the one or more fluid constituents and the relative concentrations of the one or more fluid constituents contained in the first medication container;

the peripheral medication device configured to fill the first medication container with a medication and, in response to filling the first medication container with the medication, automatically transmit, to the one or more processors external to the peripheral medication device, the medication filling information; and a writer device configured to write the encoded medication identification information to an identifier associated with the second medication container.

13. The system of claim 12, wherein writer device includes an RFID writer, and wherein the identifier includes an RFID tag.

14. A computer program product comprising at least one non-transitory computer-readable medium including program instructions that, when executed by at least one processor, cause the at least one processor to:

obtain, from a medication information source, medication identification information associated with a first medication container;

obtain, from at least one additional medication information source, additional medication information; and generate, based on the medication identification information and the additional medication information, encoded medication identification information for encoding an identifier associated with a second medication container, wherein the program instructions, when executed by the at least one processor, cause the at least one processor to obtain, from the at least one additional medication information source, the additional medication information by:

obtaining, from a fluid composition sensor, medication composition information associated with one or more fluid constituents and relative concentrations of the one or more fluid constituents contained in the first medication container, wherein the encoded medication identification information is further generated based on the medication composition information, and wherein the program instructions, when executed by the at least one processor, further cause the at least one processor to:

control the fluid composition sensor to measure the one or more fluid constituents and the relative concentrations of the one or more fluid constituents contained in the first medication container.

15. The computer program product of claim 14, wherein the instructions, when executed by the at least one processor, further cause the at least one processor to:

receive, via a user interface, a user selection of a data set of a plurality of data sets stored in an electronic database;

obtain the user selected data set from the electronic database, wherein the encoded medication identification information is further generated based on the user selected data set;

obtain system medication information associated with a patient medication order including at least one of the following: a medication filling request, patient-specific information, medication administration instructions, or any combination thereof, wherein the encoded medication identification information is further generated based on the system medication information; and receive, from a peripheral medication device used to fill the first medication container, medication filling information associated with the first medication container, wherein the encoded medication information is further generated based on the medication filling information.

16. The computer program product of claim 14, wherein the identifier includes an RFID tag.

* * * * *